US008710206B2

(12) United States Patent
Li

(10) Patent No.: US 8,710,206 B2
(45) Date of Patent: Apr. 29, 2014

(54) SOYBEAN EF1A PROMOTER AND ITS USE IN CONSTITUTIVE EXPRESSION OF TRANSGENIC GENES IN PLANTS

(75) Inventor: Zhongsen Li, Hockessin, DE (US)

(73) Assignee: E. I. du Pont de Nemours and Company, Wilmington, DE (US)

( * ) Notice: Subject to any disclaimer, the term of this patent is extended or adjusted under 35 U.S.C. 154(b) by 1149 days.

(21) Appl. No.: 12/120,281

(22) Filed: May 14, 2008

(65) Prior Publication Data

US 2008/0313776 A1 Dec. 18, 2008

Related U.S. Application Data

(60) Provisional application No. 60/944,143, filed on Jun. 15, 2007.

(51) Int. Cl.

| | |
|---|---|
| ***C12N 15/63*** | (2006.01) |
| ***C12N 15/82*** | (2006.01) |
| ***C12N 15/87*** | (2006.01) |

(52) U.S. Cl.

USPC ........ 536/24.1; 800/287; 800/278; 435/320.1

(58) Field of Classification Search

USPC ........................................................ 536/24.1

See application file for complete search history.

(56) References Cited

U.S. PATENT DOCUMENTS

| | | | | |
|---|---|---|---|---|
| 5,231,020 | A | 7/1993 | Jorgensen et al. | |
| 2002/0042931 | A1 * | 4/2002 | Kaplan et al. ................. | 800/290 |

FOREIGN PATENT DOCUMENTS

| | | |
|---|---|---|
| WO | WO98/36083 | 8/1998 |
| WO | WO99/53050 | 10/1999 |
| WO | WO 02/00904 | 1/2002 |

OTHER PUBLICATIONS

Shoemaker et al. 2006, Genbank Accession No. ED759386.*

Aguilar et al., Plant Molecular Biology, Two genes encoding the soybean translation elongation factor eEF-1x are transcribed in seedling leaves, vol. 17(3), pp. 351-360 (1991).

Axelos et al., Mol Gen Genet, The gene family encoding the *Arabidopsis thaliana* translation elongation factor EF-1x: Molecular cloning, characterization and expression, vol. 219, pp. 106-112 (1989).

Aida et al., Japan Agric. Res. Quarterly (JARQ), Efficient transgene expression in chrysanthemum, *Chrysanthemum morifolium* ramat., with the promoter of a gene for tobacco elongation factor 1 protein, vol. 39(4), pp. 269-274 (2005).

Nakane et al., Journal Gen Plant Pathol, Elicitation of primary and secondary metabolism during defense in the potato, vol. 69, pp. 378-384 (2003).

Shewmaker et al., Nucleic Acids Research, Nucleotide sequence of an EF-1x genomic clone from tomato, vol. 18(14), pp. 4276 (1990).

Wang et al., Journal of Biological Chemistry, Interaction of plant chimeric calcium/calmodulin-dependent protein kinase with a homolog of eukaryotic elongation factor-1x, vol. 274(17), pp. 12001-12008 (1999).

Kawahara et al., Eur. J. Biochem., A gene expressed preferentially in the globular stage of somatic embryogenesis encodes elongation-factor 1x in carrot, vol. 209(1), pp. 157-162 (1992).

* cited by examiner

*Primary Examiner* — Li Zheng

(57) ABSTRACT

The promoter of a soybean translation elongation factor EF1 alpha, a polypeptide that promotes the GTP-dependent binding of aminoacyl-tRNA to the A-site of ribosomes during protein biosynthesis, and fragments thereof and their use in promoting the expression of one or more heterologous nucleic acid fragments in a tissue-independent or constitutive manner in plants are described.

18 Claims, 7 Drawing Sheets

The promoter fragments sizes include the 770 bp 5UTR intron

SEQUENCE LISTING

```
<160> NUMBER OF SEQ ID NOS: 43

<210> SEQ ID NO 1
<211> LENGTH: 2181
<212> TYPE: DNA
<213> ORGANISM: Glycine max

<400> SEQUENCE: 1

gggcaatcaa attatatatg taaagcaatt acagtttatc aaactttatt tatggaaata     60

atttattatc acatttattt tggtttataa attttaaatt aaaatatcac ctaaataaaa    120

ataattttta acatgactta ttgtcctaaa taaattattt ccgtaaatta aataaaatga    180

agtttttttc tttcaaagaa tctaaatggt cataatgaga attctctaaa aaaatacata    240

atgagaataa ttatggaatt tatttattaa taaaaattaa tagcattttg atagacaatt    300

aataaaattt taaaaataac catatagaaa taataatttt tttactatcg gttccaatta    360

aaataatgat aaaaaataaa atagattatt aattgatatt gatatgaaat ttaaataaag    420

aatataatca tatattttat tgatatatga tatgatatag attaattgat attgattttg    480

atatggaatt taaaaataat ataataattg tttttattta ttaatacgtg taatcaaata    540

attctcactt tttgaatcaa tcagtgtact taaagataat atcagttgaa tatttttttat    600

ccttttacgt gtgctgtgag acattatcat caattgtgtt gtatatgata tatagatata    660

gatatataaa tatatagatt gagtgatata atatatttaa aatataaatt atatatatgt    720

tttaatatat ttttgcatat atatatatat ttgtaaaaac tagaagtatt tttcatgaga    780

taattattat cgagttgaat aagtctatta tttgtgagag ccaaccatat ttatatatgt    840

gattaaattt tatctttgtg aaattaaaaa taataaaaaa taccttaaaa tcataataat    900

agaaaaactt atatttataa tttaccatta tacttaaaaa aaattaaata aatattataa    960

atataaatac tatcgagtaa tggccgcgct agggtttttg agaaaaaatc ttcccacgca   1020

ctcaactgca ctgtacggcg tcgttttcac agccgcataa tagaagccgc gttccccaac   1080

ccttcctcac aacattctcg gaccctccag caccgtcacc caaacaaata tccacgcggt   1140

agtaggcgcg tgaaacaaac tctaatccga actacgagac gtgagaagca cgcgctttag   1200

cgagcgtttc aattgtcgct acgaaagcag agaaggatac aaacggaact agggtaaatt   1260
```

-continued agtaagggta atttcgtaaa cagaagaaaa gagttgtagc tataaataaa ccctctaacc 1320
ctcgtcgcat tacttctctt cacacctttg ttcactcttc ttctcttgcg gctagggttt 1380
tagcgcagct tcttctaggt tcgttatcta ccaccgttct atggatttta ttccttctat 1440
tcgtgtttat tctattggtt tatgttgctt gcaatatgtt ttttctgaat ctgtcgtcgt 1500
tgtcttcaat tttatccatg tttcagagat caattttgtt tgtgtagtat gtgcttattc 1560
ttcttctttt cgttcgagtt gttaataacg gtgctatggt gttttcaaaa gtgttttttt 1620
tattactttt gatttaaagt ttttttggta aggcttttat ttgcttgtta tattcaaatc 1680
tttggatcca gatcttatat aagtttttgg ttcaagaaag tttttggtta ctgatgaata 1740
gatctattaa ctgttacttt aatcgattca agctaaagtt ttttggttac tgatgaatag 1800
atctattatc tgttactttt aatcggttca agctcaagtt ttttggttac tgatgaatag 1860
atctatatac gtcacagtgt gctaaacatg cccttgtttt atctcgatct tatgtatggg 1920
agtgccataa attttgttat gtctattttt ttatctgttg gaatcatact gagtttgatg 1980
cgttacgatt gagcatacct atttttgggc ttgttgtatg gtgggtattt agatcttaat 2040
ctttttatgc ttatgaaagg ttttgtaatg acaaaggtct taatgttgtt aaacttttat 2100
ttttacttta tatggtgtgt tgatgtgtta tggttttgac aacttttttt ttttctggat 2160
ttttgcagat ttaaggaagc c 2181

<210> SEQ ID NO 2
<211> LENGTH: 1841
<212> TYPE: DNA
<213> ORGANISM: Glycine max

<400> SEQUENCE: 2
tttactatcg gttccaatta aaataatgat aaaaaataaa atagattatt aattgatatt 60
gatatgaaat ttaaataaag aatataatca tatattttat tgatatatga tatgatatag 120
attaattgat attgattttg atatggaatt taaaaataat ataataattg tttttattta 180
ttaatacgtg taatcaaata attctcactt tttgaatcaa tcagtgtact taaagataat 240
atcagttgaa tattttttat ccttttacgt gtgctgtgag acattatcat caattgtgtt 300
gtatatgata tatagatata gatatataaa tatatagatt gagtgatata atatatttaa 360
aatataaatt atatatatgt tttaatatat ttttgcatat atatatatat ttgtaaaaac 420
tagaagtatt tttcatgaga taattattat cgagttgaat aagtctatta tttgtgagag 480
ccaaccatat ttatatatgt gattaaattt tatctttgtg aaattaaaaa taataaaaaa 540
taccttaaaa tcataataat agaaaaactt atatttataa tttaccatta tacttaaaaa 600
aaattaaata aatattataa atataaatac tatcgagtaa tggccgcgct agggtttttg 660
agaaaaaatc ttcccacgca ctcaactgca ctgtacggcg tcgttttcac agccgcataa 720
tagaagccgc gttccccaac ccttcctcac aacattctcg gaccctccag caccgtcacc 780
caaacaaata tccacgcggt agtaggcgcg tgaaacaaac tctaatccga actacgagac 840
gtgagaagca cgcgctttag cgagcgtttc aattgtcgct acgaaagcag agaaggatac 900
aaacggaact agggtaaatt agtaagggta atttcgtaaa cagaagaaaa gagttgtagc 960
tataaataaa ccctctaacc ctcgtcgcat tacttctctt cacacctttg ttcactcttc 1020
ttctcttgcg gctagggttt tagcgcagct tcttctaggt tcgttatcta ccaccgttct 1080
atggatttta ttccttctat tcgtgtttat tctattggtt tatgttgctt gcaatatgtt 1140
ttttctgaat ctgtcgtcgt tgtcttcaat tttatccatg tttcagagat caattttgtt 1200

-continued

```
tgtgtagtat gtgcttattc ttcttctttt cgttcgagtt gttaataacg gtgctatggt   1260

gttttcaaaa gtgttttttt tattactttt gatttaaagt ttttttggta aggcttttat   1320

ttgcttgtta tattcaaatc tttggatcca gatcttatat aagtttttgg ttcaagaaag   1380

tttttggtta ctgatgaata gatctattaa ctgttacttt aatcgattca agctaaagtt   1440

ttttggttac tgatgaatag atctattatc tgttactttt aatcggttca agctcaagtt   1500

ttttggttac tgatgaatag atctatatac gtcacagtgt gctaaacatg cccttgtttt   1560

atctcgatct tatgtatggg agtgccataa attttgttat gtctattttt ttatctgttg   1620

gaatcatact gagtttgatg cgttacgatt gagcatacct atttttgggc ttgttgtatg   1680

gtgggtattt agatcttaat ctttttatgc ttatgaaagg ttttgtaatg acaaaggtct   1740

taatgttgtt aaacttttat ttttacttta tatggtgtgt tgatgtgtta tggttttgac   1800

aacttttttt ttttctggat ttttgcagat ttaaggaagc c                        1841
```

<210> SEQ ID NO 3
<211> LENGTH: 1642
<212> TYPE: DNA
<213> ORGANISM: Glycine max

<400> SEQUENCE: 3

```
aattctcact ttttgaatca atcagtgtac ttaaagataa tatcagttga atattttta      60

tccttttacg tgtgctgtga gacattatca tcaattgtgt tgtatatgat atatagatat    120

agatatataa atatatagat tgagtgatat aatatattta aaatataaat tatatatatg    180

ttttaatata tttttgcata tatatatata tttgtaaaaa ctagaagtat ttttcatgag    240

ataattatta tcgagttgaa taagtctatt atttgtgaga gccaaccata tttatatatg    300

tgattaaatt ttatctttgt gaaattaaaa ataataaaaa ataccttaaa atcataataa    360

tagaaaaact tatatttata atttaccatt atacttaaaa aaaattaaat aaatattata    420

aatataaata ctatcgagta atggccgcgc tagggttttt gagaaaaaat cttcccacgc    480

actcaactgc actgtacggc gtcgttttca cagccgcata atagaagccg cgttccccaa    540

cccttcctca caacattctc ggaccctcca gcaccgtcac ccaaacaaat atccacgcgg    600

tagtaggcgc gtgaaacaaa ctctaatccg aactacgaga cgtgagaagc acgcgcttta    660

gcgagcgttt caattgtcgc tacgaaagca gagaaggata caaacggaac tagggtaaat    720

tagtaagggt aatttcgtaa acagaagaaa agagttgtag ctataaataa accctctaac    780

cctcgtcgca ttacttctct tcacaccttt gttcactctt cttctcttgc ggctagggtt    840

ttagcgcagc ttcttctagg ttcgttatct accaccgttc tatggatttt attccttcta    900

ttcgtgttta ttctattggt ttatgttgct tgcaatatgt tttttctgaa tctgtcgtcg    960

ttgtcttcaa ttttatccat gtttcagaga tcaattttgt ttgtgtagta tgtgcttatt   1020

cttcttcttt tcgttcgagt tgttaataac ggtgctatgg tgttttcaaa agtgtttttt   1080

ttattacttt tgatttaaag tttttttggt aaggctttta tttgcttgtt atattcaaat   1140

ctttggatcc agatcttata taagtttttg gttcaagaaa gtttttggtt actgatgaat   1200

agatctatta actgttactt taatcgattc aagctaaagt tttttggtta ctgatgaata   1260

gatctattat ctgttacttt taatcggttc aagctcaagt tttttggtta ctgatgaata   1320

gatctatata cgtcacagtg tgctaaacat gcccttgttt tatctcgatc ttatgtatgg   1380

gagtgccata aattttgtta tgtctatttt tttatctgtt ggaatcatac tgagtttgat   1440

gcgttacgat tgagcatacc tatttttggg cttgttgtat ggtgggtatt tagatcttaa   1500
```

tctttttatg cttatgaaag gttttgtaat gacaaaggtc ttaatgttgt taaactttta 1560
tttttacttt atatggtgtg ttgatgtgtt atggttttga caactttttt tttttctgga 1620
tttttgcaga tttaaggaag cc 1642

<210> SEQ ID NO 4
<211> LENGTH: 1431
<212> TYPE: DNA
<213> ORGANISM: Glycine Max

<400> SEQUENCE: 4
ttgtaaaaac tagaagtatt tttcatgaga taattattat cgagttgaat aagtctatta 60
tttgtgagag ccaaccatat ttatatatgt gattaaattt tatctttgtg aaattaaaaa 120
taataaaaaa taccttaaaa tcataataat agaaaaactt atatttataa tttaccatta 180
tacttaaaaa aaattaaata aatattataa atataaatac tatcgagtaa tggccgcgct 240
agggtttttg agaaaaaatc ttcccacgca ctcaactgca ctgtacggcg tcgttttcac 300
agccgcataa tagaagccgc gttccccaac ccttcctcac aacattctcg gaccctccag 360
caccgtcacc caaacaaata tccacgcggt agtaggcgcg tgaaacaaac tctaatccga 420
actacgagac gtgagaagca cgcgctttag cgagcgtttc aattgtcgct acgaaagcag 480
agaaggatac aaacggaact agggtaaatt agtaagggta atttcgtaaa cagaagaaaa 540
gagttgtagc tataaataaa ccctctaacc ctcgtcgcat tacttctctt cacacctttg 600
ttcactcttc ttctcttgcg gctagggttt tagcgcagct tcttctaggt tcgttatcta 660
ccaccgttct atggatttta ttccttctat tcgtgtttat tctattggtt tatgttgctt 720
gcaatatgtt ttttctgaat ctgtcgtcgt tgtcttcaat tttatccatg tttcagagat 780
caattttgtt tgtgtagtat gtgcttattc ttcttctttt cgttcgagtt gttaataacg 840
gtgctatggt gttttcaaaa gtgttttttt tattactttt gatttaaagt ttttttggta 900
aggcttttat ttgcttgtta tattcaaatc tttggatcca gatcttatat aagtttttgg 960
ttcaagaaag tttttggtta ctgatgaata gatctattaa ctgttacttt aatcgattca 1020
agctaaagtt ttttggttac tgatgaatag atctattatc tgttactttt aatcggttca 1080
agctcaagtt ttttggttac tgatgaatag atctatatac gtcacagtgt gctaaacatg 1140
cccttgtttt atctcgatct tatgtatggg agtgccataa attttgttat gtctattttt 1200
ttatctgttg gaatcatact gagtttgatg cgttacgatt gagcatacct atttttgggc 1260
ttgttgtatg gtgggtattt agatcttaat ctttttatgc ttatgaaagg ttttgtaatg 1320
acaaaggtct taatgttgtt aaacttttat ttttacttta tatggtgtgt tgatgtgtta 1380
tggttttgac aacttttttt ttttctggat ttttgcagat ttaaggaagc c 1431

<210> SEQ ID NO 5
<211> LENGTH: 1215
<212> TYPE: DNA
<213> ORGANISM: Glycine max

<400> SEQUENCE: 5
atactatcga gtaatggccg cgctagggtt tttgagaaaa aatcttccca cgcactcaac 60
tgcactgtac ggcgtcgttt tcacagccgc ataatagaag ccgcgttccc caacccttcc 120
tcacaacatt ctcggaccct ccagcaccgt cacccaaaca aatatccacg cggtagtagg 180
cgcgtgaaac aaactctaat ccgaactacg agacgtgaga agcacgcgct ttagcgagcg 240
tttcaattgt cgctacgaaa gcagagaagg atacaaacgg aactagggta aattagtaag 300

```
ggtaatttcg taaacagaag aaaagagttg tagctataaa taaaccctct aaccctcgtc    360
gcattacttc tcttcacacc tttgttcact cttcttctct tgcggctagg gttttagcgc    420
agcttcttct aggttcgtta tctaccaccg ttctatggat tttattcctt ctattcgtgt    480
ttattctatt ggtttatgtt gcttgcaata tgtttttttct gaatctgtcg tcgttgtctt    540
caattttatc catgtttcag agatcaattt tgtttgtgta gtatgtgctt attcttcttc    600
ttttcgttcg agttgttaat aacggtgcta tggtgttttc aaaagtgttt tttttattac    660
ttttgattta aagttttttt ggtaaggctt ttatttgctt gttatattca aatctttgga    720
tccagatctt atataagttt ttggttcaag aaagtttttg gttactgatg aatagatcta    780
ttaactgtta ctttaatcga ttcaagctaa agtttttttgg ttactgatga atagatctat    840
tatctgttac ttttaatcgg ttcaagctca agtttttttgg ttactgatga atagatctat    900
atacgtcaca gtgtgctaaa catgcccttg ttttatctcg atcttatgta tgggagtgcc    960
ataaattttg ttatgtctat ttttttatct gttggaatca tactgagttt gatgcgttac   1020
gattgagcat acctattttt gggcttgttg tatggtgggt atttagatct taatcttttt   1080
atgcttatga aaggttttgt aatgacaaag gtcttaatgt tgttaaactt ttatttttac   1140
tttatatggt gtgttgatgt gttatggttt tgacaacttt tttttttttct ggatttttgc   1200
agatttaagg aagcc                                                   1215
```

<210> SEQ ID NO 6
<211> LENGTH: 1012
<212> TYPE: DNA
<213> ORGANISM: Glycine max

<400> SEQUENCE: 6

```
aactacgaga cgtgagaagc acgcgcttta gcgagcgttt caattgtcgc tacgaaagca     60
gagaaggata caaacggaac tagggtaaat tagtaagggt aatttcgtaa acagaagaaa    120
agagttgtag ctataaataa accctctaac cctcgtcgca ttacttctct tcacaccttt    180
gttcactctt cttctcttgc ggctagggtt ttagcgcagc ttcttctagg ttcgttatct    240
accaccgttc tatggatttt attccttcta ttcgtgttta ttctattggt ttatgttgct    300
tgcaatatgt tttttctgaa tctgtcgtcg ttgtcttcaa ttttatccat gtttcagaga    360
tcaattttgt ttgtgtagta tgtgcttatt cttcttcttt tcgttcgagt tgttaataac    420
ggtgctatgg tgttttcaaa agtgtttttt ttattacttt tgatttaaag tttttttggt    480
aaggctttta tttgcttgtt atattcaaat ctttggatcc agatcttata taagtttttg    540
gttcaagaaa gtttttggtt actgatgaat agatctatta actgttactt taatcgattc    600
aagctaaagt tttttggtta ctgatgaata gatctattat ctgttacttt taatcggttc    660
aagctcaagt tttttggtta ctgatgaata gatctatata cgtcacagtg tgctaaacat    720
gcccttgttt tatctcgatc ttatgtatgg gagtgccata aattttgtta tgtctatttt    780
tttatctgtt ggaatcatac tgagtttgat gcgttacgat tgagcatacc tatttttggg    840
cttgttgtat ggtgggtatt tagatcttaa tctttttatg cttatgaaag gttttgtaat    900
gacaaaggtc ttaatgttgt taaactttta tttttacttt atatggtgtg ttgatgtgtt    960
atggttttga caactttttt tttttctgga tttttgcaga tttaaggaag cc           1012
```

<210> SEQ ID NO 7
<211> LENGTH: 837
<212> TYPE: DNA
<213> ORGANISM: Glycine max

<400> SEQUENCE: 7
cctttgttca ctcttcttct cttgcggcta gggttttagc gcagcttctt ctaggttcgt 60
tatctaccac cgttctatgg attttattcc ttctattcgt gtttattcta ttggtttatg 120
ttgcttgcaa tatgtttttt ctgaatctgt cgtcgttgtc ttcaatttta tccatgtttc 180
agagatcaat tttgtttgtg tagtatgtgc ttattcttct tcttttcgtt cgagttgtta 240
ataacggtgc tatggtgttt tcaaaagtgt ttttttattt acttttgatt taaagttttt 300
ttggtaaggc ttttatttgc ttgttatatt caaatctttg gatccagatc ttatataagt 360
ttttggttca agaaagtttt tggttactga tgaatagatc tattaactgt tactttaatc 420
gattcaagct aaagtttttt ggttactgat gaatagatct attatctgtt acttttaatc 480
ggttcaagct caagtttttt ggttactgat gaatagatct atatacgtca cagtgtgcta 540
aacatgccct tgttttatct cgatcttatg tatgggagtg ccataaattt tgttatgtct 600
atttttttat ctgttggaat catactgagt ttgatgcgtt acgattgagc atacctattt 660
ttgggcttgt tgtatggtgg gtatttagat cttaatcttt ttatgcttat gaaaggtttt 720
gtaatgacaa aggtcttaat gttgttaaac ttttattttt actttatatg gtgtgttgat 780
gtgttatggt tttgacaact tttttttttt ctggattttt gcagatttaa ggaagcc 837

<210> SEQ ID NO 8
<211> LENGTH: 27
<212> TYPE: DNA
<213> ORGANISM: artificial
<220> FEATURE:
<223> OTHER INFORMATION: primer

<400> SEQUENCE: 8
ggcttcctta aatctgcaaa aatccag 27

<210> SEQ ID NO 9
<211> LENGTH: 32
<212> TYPE: DNA
<213> ORGANISM: artificial
<220> FEATURE:
<223> OTHER INFORMATION: primer

<400> SEQUENCE: 9
gggcaatcaa attatatatg taaagcaatt ac 32

<210> SEQ ID NO 10
<211> LENGTH: 30
<212> TYPE: DNA
<213> ORGANISM: artificial
<220> FEATURE:
<223> OTHER INFORMATION: primer

<400> SEQUENCE: 10
tttactatcg gttccaatta aaataatgat 30

<210> SEQ ID NO 11
<211> LENGTH: 30
<212> TYPE: DNA
<213> ORGANISM: artificial
<220> FEATURE:
<223> OTHER INFORMATION: primer

<400> SEQUENCE: 11
aattctcact ttttgaatca atcagtgtac 30

<210> SEQ ID NO 12

-continued

<211> LENGTH: 31
<212> TYPE: DNA
<213> ORGANISM: artificial
<220> FEATURE:
<223> OTHER INFORMATION: primer

<400> SEQUENCE: 12
ttgtaaaaac tagaagtatt tttcatgaga t 31

<210> SEQ ID NO 13
<211> LENGTH: 23
<212> TYPE: DNA
<213> ORGANISM: artificial
<220> FEATURE:
<223> OTHER INFORMATION: primer

<400> SEQUENCE: 13
atactatcga gtaatggccg cgc 23

<210> SEQ ID NO 14
<211> LENGTH: 24
<212> TYPE: DNA
<213> ORGANISM: artificial
<220> FEATURE:
<223> OTHER INFORMATION: primer

<400> SEQUENCE: 14
aactacgaga cgtgagaagc acgc 24

<210> SEQ ID NO 15
<211> LENGTH: 26
<212> TYPE: DNA
<213> ORGANISM: artificial
<220> FEATURE:
<223> OTHER INFORMATION: primer

<400> SEQUENCE: 15
cctttgttca ctcttcttct cttgcg 26

<210> SEQ ID NO 16
<211> LENGTH: 770
<212> TYPE: DNA
<213> ORGANISM: Glycine max

<400> SEQUENCE: 16
gttcgttatc taccaccgtt ctatggattt tattccttct attcgtgttt attctattgg 60
tttatgttgc ttgcaatatg ttttttctga atctgtcgtc gttgtcttca attttatcca 120
tgtttcagag atcaattttg tttgtgtagt atgtgcttat tcttcttctt ttcgttcgag 180
ttgttaataa cggtgctatg gtgttttcaa aagtgttttt tttattactt ttgatttaaa 240 gttttttttgg taaggctttt atttgcttgt tatattcaaa tctttggatc cagatcttat 300
ataagttttt ggttcaagaa agtttttggt tactgatgaa tagatctatt aactgttact 360
ttaatcgatt caagctaaag ttttttggtt actgatgaat agatctatta tctgttactt 420
ttaatcggtt caagctcaag ttttttggtt actgatgaat agatctatat acgtcacagt 480
gtgctaaaca tgcccttgtt ttatctcgat cttatgtatg ggagtgccat aaattttgtt 540
atgtctattt ttttatctgt tggaatcata ctgagtttga tgcgttacga ttgagcatac 600
ctatttttgg gcttgttgta tggtgggtat ttagatctta atctttttat gcttatgaaa 660
ggttttgtaa tgacaaaggt cttaatgttg ttaaactttt atttttactt tatatggtgt 720
gttgatgtgt tatggttttg acaacttttt ttttttctgg atttttgcag 770

-continued

<210> SEQ ID NO 17
<211> LENGTH: 54
<212> TYPE: DNA
<213> ORGANISM: Glycine max

<400> SEQUENCE: 17
cctttgttca ctcttcttct cttgcggcta gggttttagc gcagcttctt ctag 54

<210> SEQ ID NO 18
<211> LENGTH: 13
<212> TYPE: DNA
<213> ORGANISM: Glycien Max

<400> SEQUENCE: 18
atttaaggaa gcc 13

<210> SEQ ID NO 19
<211> LENGTH: 41
<212> TYPE: DNA
<213> ORGANISM: artificial
<220> FEATURE:
<223> OTHER INFORMATION: primer

<400> SEQUENCE: 19
acttcccggg caatcaaatt atatatgtaa agcaattaca g 41

<210> SEQ ID NO 20
<211> LENGTH: 35
<212> TYPE: DNA
<213> ORGANISM: artificial
<220> FEATURE:
<223> OTHER INFORMATION: primer

<400> SEQUENCE: 20
tagtccatgg cttccttaaa tctgcaaaaa tccag 35

<210> SEQ ID NO 21
<211> LENGTH: 1724
<212> TYPE: DNA
<213> ORGANISM: Glycine max

<400> SEQUENCE: 21
cctttgttca ctcttcttct cttgcggcta gggttttagc gcagcttctt ctagatttaa 60
ggaagatggg taaggaaaag gttcacatca gtattgtggt cattggccat gtcgactctg 120
ggaaatccac taccactggt cacctgattt acaagcttgg aggcattgac aagcgtgtta 180
ttgagaggtt tgagaaggaa gctgctgaga tgaacaagag gtctttcaag tatgcctggg 240
tgctggacaa acttaaggct gagcgtgaaa gaggaatcac cattgatatt gctttgtgga 300
agtttgaaac aacaaagtat tattgcacag ttattgatgc gcctggacat agggatttca 360
ttaagaatat gattactggg acatcccaag ctgactgtgc tgttcttatc attgattcga 420
ccactggtgg ttttgaagct ggtatttcca aggatggaca gactcgtgaa catgctctgc 480
tttcattcac ccttggtgtg aaacagatga tttgctgctg taacaaaatg gatgctacta 540
cacccaagta ttccaaggcc aggtatgatg aaattgtgaa ggaagtctct tcctacttga 600
agaaagtagg atacaaccct gacaagattc cttttgttcc tatctctggt tttgagggag 660
acaacatgat tgagaggtcc acaaaccttg actggtacaa gggtccaact ctgcttgatg 720
cacttgacca gattagtgag cccaagaggc cctctgacaa gcccctcagg cttcccc ttc 780 aggatgtgta caagattgga ggtattggaa ctgtgccagt gggacgtgtt gagaccggtg 840

-continued

```
tcttgaagcc tggaatggtg gtgacttttg caccaactgg actgacaact gaagtcaagt    900

ctgtggagat gcaccatgaa tctcttacag aggcacatcc tggtgacaat gtgggattca    960

atgttaagaa tgttgctgtt aaggatttga agcgtggtta tgttgcctca aactcaaagg   1020

atgaccctgc aaaggaggct gctaacttca cagcccaagt catcatcatg aaccaccctg   1080

gtcagattgg aaatggctat gcccctgtcc tcgactgcca cacttctcac attgctgtca   1140

agtttgctga actcatgacc aagattgaca ggcgatccgg caaagagctt gagaaggagc   1200

ccaagttttt gaagaacggt gatgctggtt ttgttaagat gattccaacc aaacccatgg   1260

ttgttgaaac tttctccgag tatcctccac ttggtaggtt tgctgttagg gacatgcgtc   1320

aaactgttgc tgtgggagtc atcaagaacg ttgagaagaa ggatcctacc ggagccaagg   1380

tcaccaaggc tgcccagaag aagaagtgaa tcgtgcgggc tggttcatca ggggatgttg   1440

gttacaataa atgttggttt cttttctgta ctcttgtgtc ttcttttcta ggtagcttgt   1500

ttttcggaca aagtttgaag tctccaccat catctcgcaa ctgttgttcc cagaactggg   1560

ttcttgatcg acggtggcaa aattgctttt atttatctgt gttttaatgt gttgtgtttg   1620

tcggaacccc tgattacatt tttgttaagc gcagcgagtt tcaggacttt gctgcgttgt   1680

gttgctttgg tttattaaat gtcaactttc tatttgtagt gttc                    1724
```

<210> SEQ ID NO 22
<211> LENGTH: 447
<212> TYPE: PRT
<213> ORGANISM: Glycine max

<400> SEQUENCE: 22

```
Met Gly Lys Glu Lys Val His Ile Ser Ile Val Val Ile Gly His Val
1               5                   10                  15

Asp Ser Gly Lys Ser Thr Thr Thr Gly His Leu Ile Tyr Lys Leu Gly
            20                  25                  30

Gly Ile Asp Lys Arg Val Ile Glu Arg Phe Glu Lys Glu Ala Ala Glu
        35                  40                  45

Met Asn Lys Arg Ser Phe Lys Tyr Ala Trp Val Leu Asp Lys Leu Lys
    50                  55                  60

Ala Glu Arg Glu Arg Gly Ile Thr Ile Asp Ile Ala Leu Trp Lys Phe
65                  70                  75                  80

Glu Thr Thr Lys Tyr Tyr Cys Thr Val Ile Asp Ala Pro Gly His Arg
                85                  90                  95

Asp Phe Ile Lys Asn Met Ile Thr Gly Thr Ser Gln Ala Asp Cys Ala
            100                 105                 110

Val Leu Ile Ile Asp Ser Thr Thr Gly Gly Phe Glu Ala Gly Ile Ser
        115                 120                 125

Lys Asp Gly Gln Thr Arg Glu His Ala Leu Leu Ser Phe Thr Leu Gly
    130                 135                 140

Val Lys Gln Met Ile Cys Cys Cys Asn Lys Met Asp Ala Thr Thr Pro
145                 150                 155                 160

Lys Tyr Ser Lys Ala Arg Tyr Asp Glu Ile Val Lys Glu Val Ser Ser
                165                 170                 175

Tyr Leu Lys Lys Val Gly Tyr Asn Pro Asp Lys Ile Pro Phe Val Pro
            180                 185                 190

Ile Ser Gly Phe Glu Gly Asp Asn Met Ile Glu Arg Ser Thr Asn Leu
        195                 200                 205

Asp Trp Tyr Lys Gly Pro Thr Leu Leu Asp Ala Leu Asp Gln Ile Ser
    210                 215                 220
```

```
Glu Pro Lys Arg Pro Ser Asp Lys Pro Leu Arg Leu Pro Leu Gln Asp
225                 230                 235                 240

Val Tyr Lys Ile Gly Gly Ile Gly Thr Val Pro Val Gly Arg Val Glu
                245                 250                 255

Thr Gly Val Leu Lys Pro Gly Met Val Val Thr Phe Ala Pro Thr Gly
            260                 265                 270

Leu Thr Thr Glu Val Lys Ser Val Glu Met His His Glu Ser Leu Thr
        275                 280                 285

Glu Ala His Pro Gly Asp Asn Val Gly Phe Asn Val Lys Asn Val Ala
    290                 295                 300

Val Lys Asp Leu Lys Arg Gly Tyr Val Ala Ser Asn Ser Lys Asp Asp
305                 310                 315                 320

Pro Ala Lys Glu Ala Ala Asn Phe Thr Ala Gln Val Ile Ile Met Asn
                325                 330                 335

His Pro Gly Gln Ile Gly Asn Gly Tyr Ala Pro Val Leu Asp Cys His
            340                 345                 350

Thr Ser His Ile Ala Val Lys Phe Ala Glu Leu Met Thr Lys Ile Asp
        355                 360                 365

Arg Arg Ser Gly Lys Glu Leu Glu Lys Glu Pro Lys Phe Leu Lys Asn
    370                 375                 380

Gly Asp Ala Gly Phe Val Lys Met Ile Pro Thr Lys Pro Met Val Val
385                 390                 395                 400

Glu Thr Phe Ser Glu Tyr Pro Pro Leu Gly Arg Phe Ala Val Arg Asp
                405                 410                 415

Met Arg Gln Thr Val Ala Val Gly Val Ile Lys Asn Val Glu Lys Lys
            420                 425                 430

Asp Pro Thr Gly Ala Lys Val Thr Lys Ala Ala Gln Lys Lys Lys
        435                 440                 445


<210> SEQ ID NO 23
<211> LENGTH: 5465
<212> TYPE: DNA
<213> ORGANISM: artificial
<220> FEATURE:
<223> OTHER INFORMATION: vector

<400> SEQUENCE: 23

catggcccac agcaagcacg gcctgaagga ggagatgacc atgaagtacc acatggaggg     60

ctgcgtgaac ggccacaagt tcgtgatcac cggcgagggc atcggctacc ccttcaaggg    120

caagcagacc atcaacctgt gcgtgatcga gggcggcccc ctgcccttca gcgaggacat    180

cctgagcgcc ggcttcaagt acggcgaccg gatcttcacc gagtaccccc aggacatcgt    240

ggactacttc aagaacagct gccccgccgg ctacacctgg ggccggagct tcctgttcga    300

ggacggcgcc gtgtgcatct gtaacgtgga catcaccgtg agcgtgaagg agaactgcat    360

ctaccacaag agcatcttca acggcgtgaa cttccccgcc gacggccccg tgatgaagaa    420

gatgaccacc aactgggagg ccagctgcga gaagatcatg cccgtgccta agcagggcat    480

cctgaagggc gacgtgagca tgtacctgct gctgaaggac ggcggccggt accggtgcca    540

gttcgacacc gtgtacaagg ccaagagcgt gcccagcaag atgcccgagt ggcacttcat    600

ccagcacaag ctgctgcggg aggaccggag cgacgccaag aaccagaagt ggcagctgac    660

cgagcacgcc atcgccttcc ccagcgccct ggcctgagag ctcgaatttc cccgatcgtt    720

caaacatttg gcaataaagt ttcttaagat tgaatcctgt tgccggtctt gcgatgatta    780

tcatataatt tctgttgaat tacgttaagc atgtaataat taacatgtaa tgcatgacgt    840
```

-continued

```
tatttatgag atgggttttt atgattagag tcccgcaatt atacatttaa tacgcgatag    900
aaaacaaaat atagcgcgca aactaggata aattatcgcg cgcggtgtca tctatgttac    960
tagatcggga attctagtgg ccggcccagc tgatatccat cacactggcg gccgcactcg   1020
actgaattgg ttccggcgcc agcctgcttt tttgtacaaa gttggcatta taaaaaagca   1080
ttgcttatca atttgttgca acgaacaggt cactatcagt caaaataaaa tcattatttg   1140
gggcccgagc ttaagtaact aactaacagg aagagtttgt agaaacgcaa aaaggccatc   1200
cgtcaggatg gccttctgct tagtttgatg cctggcagtt tatggcgggc gtcctgcccg   1260
ccaccctccg ggccgttgct tcacaacgtt caaatccgct cccggcggat ttgtcctact   1320
caggagagcg ttcaccgaca aacaacagat aaaacgaaag gcccagtctt ccgactgagc   1380
ctttcgtttt atttgatgcc tggcagttcc ctactctcgc ttagtagtta gacgtccccg   1440
agatccatgc tagcggtaat acggttatcc acagaatcag gggataacgc aggaaagaac   1500
atgtgagcaa aaggccagca aaaggccagg aaccgtaaaa aggccgcgtt gctggcgttt   1560
ttccataggc tccgcccccc tgacgagcat cacaaaaatc gacgctcaag tcagaggtgg   1620
cgaaacccga caggactata aagataccag gcgtttcccc ctggaagctc cctcgtgcgc   1680
tctcctgttc cgaccctgcc gcttaccgga tacctgtccg cctttctccc ttcgggaagc   1740
gtggcgcttt ctcatagctc acgctgtagg tatctcagtt cggtgtaggt cgttcgctcc   1800
aagctgggct gtgtgcacga accccccgtt cagcccgacc gctgcgcctt atccggtaac   1860
tatcgtcttg agtccaaccc ggtaagacac gacttatcgc cactggcagc agccactggt   1920
aacaggatta gcagagcgag gtatgtaggc ggtgctacag agttcttgaa gtggtggcct   1980
aactacggct acactagaag aacagtattt ggtatctgcg ctctgctgaa gccagttacc   2040
ttcggaaaaa gagttggtag ctcttgatcc ggcaaacaaa ccaccgctgg tagcggtggt   2100
tttttgttt gcaagcagca gattacgcgc agaaaaaaag gatctcaaga agatcctttg    2160
atcttttcta cggggtctga cgctcagtgg aacggggccc aatctgaata atgttacaac   2220
caattaacca attctgatta gaaaaactca tcgagcatca aatgaaactg caatttattc   2280
atatcaggat tatcaatacc atatttttga aaaagccgtt tctgtaatga aggagaaaac   2340
tcaccgaggc agttccatag gatggcaaga tcctggtatc ggtctgcgat tccgactcgt   2400
ccaacatcaa tacaacctat taatttcccc tcgtcaaaaa taaggttatc aagtgagaaa   2460
tcaccatgag tgacgactga atccggtgag aatggcaaaa gtttatgcat ttctttccag   2520
acttgttcaa caggccagcc attacgctcg tcatcaaaat cactcgcatc aaccaaaccg   2580
ttattcattc gtgattgcgc ctgagcgaga cgaaatacgc gatcgctgtt aaaaggacaa   2640
ttacaaacag gaatcgaatg caaccggcgc aggaacactg ccagcgcatc aacaatattt   2700
tcacctgaat caggatattc ttctaatacc tggaatgctg tttttccggg gatcgcagtg   2760
gtgagtaacc atgcatcatc aggagtacgg ataaaatgct tgatggtcgg aagaggcata   2820
aattccgtca gccagtttag tctgaccatc tcatctgtaa catcattggc aacgctacct   2880
ttgccatgtt tcagaaacaa ctctggcgca tcgggcttcc catacaagcg atagattgtc   2940
gcacctgatt gcccgacatt atcgcgagcc catttatacc catataaatc agcatccatg   3000
ttggaattta atcgcggcct cgacgtttcc cgttgaatat ggctcataac accccttgta   3060
ttactgttta tgtaagcaga cagttttatt gttcatgatg atatattttt atcttgtgca   3120
atgtaacatc agagattttg agacacgggc cagagctgca gctggatggc aaataatgat   3180
tttattttga ctgatagtga cctgttcgtt gcaacaaatt gataagcaat gctttcttat   3240
```

```
aatgccaact ttgtacaaga aagctgggtc tagatatctc gacccgggca atcaaattat   3300

atatgtaaag caattacagt ttatcaaact ttatttatgg aaataattta ttatcacatt   3360

tattttggtt tataaatttt aaattaaaat atcacctaaa taaaaataat ttttaacatg   3420

acttattgtc ctaaataaat tatttccgta aattaaataa aatgaagttt ttttctttca   3480

aagaatctaa atggtcataa tgagaattct ctaaaaaaat acataatgag aataattatg   3540

gaatttattt attaataaaa attaatagca ttttgataga caattaataa aattttaaaa   3600

ataaccatat agaaataata attttttttac tatcggttcc aattaaaata atgataaaaa   3660

ataaaataga ttattaattg atattgatat gaaatttaaa taaagaatat aatcatatat   3720

tttattgata tatgatatga tatagattaa ttgatattga ttttgatatg gaatttaaaa   3780

ataatataat aattgttttt atttattaat acgtgtaatc aaataattct cactttttga   3840

atcaatcagt gtacttaaag ataatatcag ttgaatattt tttatccttt tacgtgtgct   3900

gtgagacatt atcatcaatt gtgttgtata tgatatatag atatagatat ataaatatat   3960

agattgagtg atataatata tttaaaatat aaattatata tatgttttaa tatatttttg   4020

catatatata tatatttgta aaaactagaa gtatttttca tgagataatt attatcgagt   4080

tgaataagtc tattatttgt gagagccaac catatttata tatgtgatta aattttatct   4140

ttgtgaaatt aaaaataata aaaaatacct taaaatcata ataatagaaa aacttatatt   4200

tataatttac cattatactt aaaaaaaatt aaataaatat tataaatata aatactatcg   4260

agtaatggcc gcgctagggt ttttgagaaa aaatcttccc acgcactcaa ctgcactgta   4320

cggcgtcgtt ttcacagccg cataatagaa gccgcgttcc ccaacccttc ctcacaacat   4380

tctcggaccc tccagcaccg tcacccaaac aaatatccac gcggtagtag gcgcgtgaaa   4440

caaactctaa tccgaactac gagacgtgag aagcacgcgc tttagcgagc gtttcaattg   4500

tcgctacgaa agcagagaag gatacaaacg gaactagggt aaattagtaa gggtaatttc   4560

gtaaacagaa gaaaagagtt gtagctataa ataaaccctc taaccctcgt cgcattactt   4620

ctcttcacac ctttgttcac tcttcttctc ttgcggctag ggttttagcg cagcttcttc   4680

taggttcgtt atctaccacc gttctatgga ttttattcct tctattcgtg tttattctat   4740

tggtttatgt tgcttgcaat atgtttttttc tgaatctgtc gtcgttgtct tcaattttat   4800

ccatgtttca gagatcaatt ttgtttgtgt agtatgtgct tattcttctt cttttcgttc   4860

gagttgttaa taacggtgct atggtgtttt caaaagtgtt ttttttatta cttttgattt   4920

aaagtttttt tggtaaggct tttatttgct tgttatattc aaatctttgg atccagatct   4980

tatataagtt tttggttcaa gaaagttttt ggttactgat gaatagatct attaactgtt   5040

actttaatcg attcaagcta aagttttttg gttactgatg aatagatcta ttatctgtta   5100

cttttaatcg gttcaagctc aagttttttg gttactgatg aatagatcta tatacgtcac   5160

agtgtgctaa acatgccctt gttttatctc gatcttatgt atgggagtgc cataaatttt   5220

gttatgtcta ttttttatc tgttggaatc atactgagtt tgatgcgtta cgattgagca   5280

tacctatttt tgggcttgtt gtatggtggg tatttagatc ttaatctttt tatgcttatg   5340

aaaggttttg taatgacaaa ggtcttaatg ttgttaaact tttattttta ctttatatgg   5400

tgtgttgatg tgttatggtt ttgacaactt ttttttttc tggatttttg cagatttaag   5460

gaagc                                                               5465
```

<210> SEQ ID NO 24
<211> LENGTH: 9768
<212> TYPE: DNA

-continued

<213> ORGANISM: artificial
<220> FEATURE:
<223> OTHER INFORMATION: vector

<400> SEQUENCE: 24
tttgtacaaa cttgtgattc ttccttacca atcatactaa ttattttggg ttaaatatta 60
atcattattt ttaagatatt aattaagaaa ttaaaagatt ttttaaaaaa atgtataaaa 120
ttatattatt catgattttt catacatttg attttgataa taaatatatt ttttttaatt 180
tcttaaaaaa tgttgcaaga cacttattag acatagtctt gttctgttta caaaagcatt 240
catcatttaa tacattaaaa aatatttaat actaacagta gaatcttctt gtgagtggtg 300
tgggagtagg caacctggca ttgaaacgag agaaagagag tcagaaccag aagacaaata 360
aaaagtatgc aacaaacaaa tcaaaatcaa agggcaaagg ctggggttgg ctcaattggt 420
tgctacattc aattttcaac tcagtcaacg gttgagattc actctgactt ccccaatcta 480
agccgcggat gcaaacggtt gaatctaacc cacaatccaa tctcgttact taggggcttt 540
tccgtcatta actcacccct gccacccggt ttccctataa attggaactc aatgctcccc 600
tctaaactcg tatcgcttca gagttgagac caagacacac tcgttcatat atctctctgc 660
tcttctcttc tcttctacct ctcaaggtac ttttcttctc cctctaccaa atcctagatt 720
ccgtggttca atttcggatc ttgcacttct ggtttgcttt gccttgcttt ttcctcaact 780
gggtccatct aggatccatg tgaaactcta ctctttcttt aatatctgcg gaatacgcgt 840
ttgactttca gatctagtcg aaatcatttc ataattgcct ttctttcttt tagcttatga 900
gaaataaaat cacttttttt ttatttcaaa ataaaccttg ggccttgtgc tgactgagat 960
ggggtttggt gattacagaa ttttagcgaa ttttgtaatt gtacttgttt gtctgtagtt 1020
ttgttttgtt ttcttgtttc tcatacattc cttaggcttc aattttattc gagtataggt 1080
cacaatagga attcaaactt tgagcagggg aattaatccc ttccttcaaa tccagtttgt 1140
ttgtatatat gtttaaaaaa tgaaactttt gctttaaatt ctattataac tttttttatg 1200
gctgaaattt ttgcatgtgt ctttgctctc tgttgtaaat ttactgttta ggtactaact 1260
ctaggcttgt tgtgcagttt ttgaagtata accatgccac acaacacaat ggcggccacc 1320
gcttccagaa ccacccgatt ctcttcttcc tcttcacacc ccaccttccc caaacgcatt 1380
actagatcca ccctccctct ctctcatcaa accctcacca aacccaacca cgctctcaaa 1440
atcaaatgtt ccatctccaa accccccacg gcggcgccct tcaccaagga agcgccgacc 1500
acggagccct tcgtgtcacg gttcgcctcc ggcgaacctc gcaagggcgc ggacatcctt 1560
gtggaggcgc tggagaggca gggcgtgacg acggtgttcg cgtaccccgg cggtgcgtcg 1620
atggagatcc accaggcgct cacgcgctcc gccgccatcc gcaacgtgct cccgcgccac 1680
gagcagggcg gcgtcttcgc cgccgaaggc tacgcgcgtt cctccggcct ccccggcgtc 1740
tgcattgcca cctccggccc cggcgccacc aacctcgtga gcggcctcgc cgacgcttta 1800
atggacagcg tcccagtcgt cgccatcacc ggccaggtcg cccgccggat gatcggcacc 1860
gacgccttcc aagaaacccc gatcgtggag gtgagcagat ccatcacgaa gcacaactac 1920
ctcatcctcg acgtcgacga catcccccgc gtcgtcgccg aggctttctt cgtcgccacc 1980
tccggccgcc ccggtccggt cctcatcgac attcccaaag acgttcagca gcaactcgcc 2040
gtgcctaatt gggacgagcc cgttaacctc cccggttacc tcgccaggct gcccaggccc 2100
cccgccgagg cccaattgga acacattgtc agactcatca tggaggccca aaagcccgtt 2160
ctctacgtcg gcggtggcag tttgaattcc agtgctgaat tgaggcgctt tgttgaactc 2220

-continued

```
actggtattc ccgttgctag cactttaatg ggtcttggaa cttttcctat tggtgatgaa   2280
tattcccttc agatgctggg tatgcatggt actgtttatg ctaactatgc tgttgacaat   2340
agtgatttgt tgcttgcctt tggggtaagg tttgatgacc gtgttactgg gaagcttgag   2400
gcttttgcta gtagggctaa gattgttcac attgatattg attctgccga gattgggaag   2460
aacaagcagg cgcacgtgtc ggtttgcgcg gatttgaagt tggccttgaa gggaattaat   2520
atgattttgg aggagaaagg agtggagggt aagtttgatc ttggaggttg gagagaagag   2580
attaatgtgc agaaacacaa gtttccattg ggttacaaga cattccagga cgcgatttct   2640
ccgcagcatg ctatcgaggt tcttgatgag ttgactaatg gagatgctat tgttagtact   2700
ggggttgggc agcatcaaat gtgggctgcg cagttttaca agtacaagag accgaggcag   2760
tggttgacct caggggggtct tggagccatg ggttttggat tgcctgcggc tattggtgct   2820
gctgttgcta accctggggc tgttgtggtt gacattgatg gggatggtag tttcatcatg   2880
aatgttcagg agttggccac tataagagtg gagaatctcc cagttaagat attgttgttg   2940
aacaatcagc atttgggtat ggtggttcag ttggaggata ggttctacaa gtccaataga   3000
gctcacacct atcttggaga tccgtctagc gagagcgaga tattcccaaa catgctcaag   3060
tttgctgatg cttgtgggat accggcagcg cgagtgacga agaaggaaga gcttagagcg   3120
gcaattcaga gaatgttgga cacccctggc ccctaccttc ttgatgtcat tgtgccccat   3180
caggagcatg tgttgccgat gattcccagt aatggatcct tcaaggatgt gataactgag   3240
ggtgatggta gaacgaggta ctgattgcct agaccaaatg ttccttgatg cttgttttgt   3300
acaatatata taagataatg ctgtcctagt tgcaggattt ggcctgtggt gagcatcata   3360
gtctgtagta gttttggtag caagacattt tattttcctt ttatttaact tactacatgc   3420
agtagcatct atctatctct gtagtctgat atctcctgtt gtctgtattg tgccgttgga   3480
ttttttgctg tagtgagact gaaaatgatg tgctagtaat aatatttctg ttagaaatct   3540
aagtagagaa tctgttgaag aagtcaaaag ctaatggaat caggttacat attcaatgtt   3600
tttctttttt tagcggttgg tagacgtgta gattcaactt ctcttggagc tcacctaggc   3660
aatcagtaaa atgcatattc ctttttttaac ttgccattta tttactttta gtggaaattg   3720
tgaccaattt gttcatgtag aacggatttg gaccattgcg tccacaaaac gtctcttttg   3780
ctcgatcttc acaaagcgat accgaaatcc agagatagtt ttcaaaagtc agaaatggca   3840
aagttataaa tagtaaaaca gaatagatgc tgtaatcgac ttcaataaca agtggcatca   3900
cgtttctagt tctagacccg ggtaccggcg cgcccgatca tccggatata gttcctcctt   3960
tcagcaaaaa acccctcaag acccgtttag aggccccaag gggttatgct agttattgct   4020
cagcggtggc agcagccaac tcagcttcct ttcgggcttt gttagcagcc ggatcgatcc   4080
aagctgtacc tcactattcc tttgccctcg gacgagtgct ggggcgtcgg tttccactat   4140
cggcgagtac ttctacacag ccatcggtcc agacggccgc gcttctgcgg gcgatttgtg   4200
tacgcccgac agtcccggct ccggatcgga cgattgcgtc gcatcgaccc tgcgcccaag   4260
ctgcatcatc gaaattgccg tcaaccaagc tctgatagag ttggtcaaga ccaatgcgga   4320
gcatatacgc ccggagccgc ggcgatcctg caagctccgg atgcctccgc tcgaagtagc   4380
gcgtctgctg ctccatacaa gccaaccacg gcctccagaa gaagatgttg gcgacctcgt   4440
attgggaatc cccgaacatc gcctcgctcc agtcaatgac cgctgttatg cggccattgt   4500
ccgtcaggac attgttggag ccgaaatccg cgtgcacgag gtgccggact tcggggcagt   4560
cctcggccca aagcatcagc tcatcgagag cctgcgcgac ggacgcactg acggtgtcgt   4620
```

-continued

```
ccatcacagt ttgccagtga tacacatggg gatcagcaat cgcgcatatg aaatcacgcc   4680
atgtagtgta ttgaccgatt ccttgcggtc cgaatgggcc gaacccgctc gtctggctaa   4740
gatcggccgc agcgatcgca tccatagcct ccgcgaccgg ctgcagaaca gcgggcagtt   4800
cggtttcagg caggtcttgc aacgtgacac cctgtgcacg gcgggagatg caataggtca   4860
ggctctcgct gaattcccca atgtcaagca cttccggaat cgggagcgcg gccgatgcaa   4920
agtgccgata aacataacga tctttgtaga aaccatcggc gcagctattt acccgcagga   4980
catatccacg ccctcctaca tcgaagctga aagcacgaga ttcttcgccc tccgagagct   5040
gcatcaggtc ggagacgctg tcgaactttt cgatcagaaa cttctcgaca gacgtcgcgg   5100
tgagttcagg cttttccatg ggtatatctc cttcttaaag ttaaacaaaa ttatttctag   5160
agggaaaccg ttgtggtctc cctatagtga gtcgtattaa tttcgcggga tcgagatctg   5220
atcaacctgc attaatgaat cggccaacgc gcggggagag gcggtttgcg tattgggcgc   5280
tcttccgctt cctcgctcac tgactcgctg cgctcggtcg ttcggctgcg gcgagcggta   5340
tcagctcact caaaggcggt aatacggtta tccacagaat caggggataa cgcaggaaag   5400
aacatgtgag caaaaggcca gcaaaaggcc aggaaccgta aaaaggccgc gttgctggcg   5460
tttttccata ggctccgccc ccctgacgag catcacaaaa atcgacgctc aagtcagagg   5520
tggcgaaacc cgacaggact ataaagatac caggcgtttc cccctggaag ctccctcgtg   5580
cgctctcctg ttccgaccct gccgcttacc ggatacctgt ccgcctttct cccttcggga   5640
agcgtggcgc tttctcaatg ctcacgctgt aggtatctca gttcggtgta ggtcgttcgc   5700
tccaagctgg gctgtgtgca cgaacccccc gttcagcccg accgctgcgc cttatccggt   5760
aactatcgtc ttgagtccaa cccggtaaga cacgacttat cgccactggc agcagccact   5820
ggtaacagga ttagcagagc gaggtatgta ggcggtgcta cagagttctt gaagtggtgg   5880
cctaactacg gctacactag aaggacagta tttggtatct gcgctctgct gaagccagtt   5940
accttcggaa aaagagttgg tagctcttga tccggcaaac aaaccaccgc tggtagcggt   6000
ggtttttttg tttgcaagca gcagattacg cgcagaaaaa aaggatctca agaagatcct   6060
ttgatctttt ctacggggtc tgacgctcag tggaacgaaa actcacgtta agggattttg   6120
gtcatgacat taacctataa aaataggcgt atcacgaggc cctttcgtct cgcgcgtttc   6180
ggtgatgacg gtgaaaacct ctgacacatg cagctcccgg agacggtcac agcttgtctg   6240
taagcggatg ccgggagcag acaagcccgt cagggcgcgt cagcgggtgt tggcgggtgt   6300
cggggctggc ttaactatgc ggcatcagag cagattgtac tgagagtgca ccatatggac   6360
atattgtcgt tagaacgcgg ctacaattaa tacataacct tatgtatcat acacatacga   6420
tttaggtgac actatagaac ggcgcgccgg taccgggccc cccctcgagt gcggccgcaa   6480
gcttgtcgac ggagatcacc actttgtaca agaaagctgg gtctagatat ctcgacccgg   6540
gcaatcaaat tatatatgta aagcaattac agtttatcaa actttattta tggaaataat   6600
ttattatcac atttattttg gtttataaat tttaaattaa aatatcacct aaataaaaat   6660
aatttttaac atgacttatt gtcctaaata aattatttcc gtaaattaaa taaaatgaag   6720
tttttttctt tcaaagaatc taaatggtca taatgagaat tctctaaaaa aatacataat   6780
gagaataatt atggaattta tttattaata aaaattaata gcattttgat agacaattaa   6840
taaaatttta aaaataacca tatagaaata ataatttttt tactatcggt tccaattaaa   6900
ataatgataa aaaataaaat agattattaa ttgatattga tatgaaattt aaataaagaa   6960
tataatcata tattttattg atatatgata tgatatagat taattgatat tgattttgat   7020
```

```
atggaattta aaaataatat aataattgtt tttatttatt aatacgtgta atcaaataat   7080
tctcactttt tgaatcaatc agtgtactta aagataatat cagttgaata tttttttatcc  7140
ttttacgtgt gctgtgagac attatcatca attgtgttgt atatgatata tagatataga   7200
tatataaata tatagattga gtgatataat atatttaaaa tataaattat atatatgttt   7260
taatatattt ttgcatatat atatatattt gtaaaaacta gaagtatttt tcatgagata   7320
attattatcg agttgaataa gtctattatt tgtgagagcc aaccatattt atatatgtga   7380
ttaaatttta tctttgtgaa attaaaaata ataaaaaata ccttaaaatc ataataatag   7440
aaaaacttat atttataatt taccattata cttaaaaaaa attaaataaa tattataaat   7500
ataaatacta tcgagtaatg gccgcgctag ggtttttgag aaaaaatctt cccacgcact   7560
caactgcact gtacggcgtc gttttcacag ccgcataata gaagccgcgt tccccaaccc   7620
ttcctcacaa cattctcgga ccctccagca ccgtcaccca aacaaatatc cacgcggtag   7680
taggcgcgtg aaacaaactc taatccgaac tacgagacgt gagaagcacg cgctttagcg   7740
agcgtttcaa ttgtcgctac gaaagcagag aaggatacaa acggaactag ggtaaattag   7800
taagggtaat ttcgtaaaca gaagaaaaga gttgtagcta taaataaacc ctctaaccct   7860
cgtcgcatta cttctcttca cacctttgtt cactcttctt ctcttgcggc tagggtttta   7920
gcgcagcttc ttctaggttc gttatctacc accgttctat ggattttatt ccttctattc   7980
gtgtttattc tattggttta tgttgcttgc aatatgtttt ttctgaatct gtcgtcgttg   8040
tcttcaattt tatccatgtt tcagagatca attttgtttg tgtagtatgt gcttattctt   8100
cttcttttcg ttcgagttgt taataacggt gctatggtgt tttcaaaagt gtttttttta   8160
ttacttttga tttaaagttt ttttggtaag gcttttattt gcttgttata ttcaaatctt   8220
tggatccaga tcttatataa gtttttggtt caagaaagtt tttggttact gatgaataga   8280
tctattaact gttactttaa tcgattcaag ctaaagtttt ttggttactg atgaatagat   8340
ctattatctg ttacttttaa tcggttcaag ctcaagtttt ttggttactg atgaatagat   8400
ctatatacgt cacagtgtgc taaacatgcc cttgttttat ctcgatctta tgtatgggag   8460
tgccataaat tttgttatgt ctattttttt atctgttgga atcatactga gtttgatgcg   8520
ttacgattga gcatacctat ttttgggctt gttgtatggt gggtatttag atcttaatct   8580
ttttatgctt atgaaaggtt ttgtaatgac aaaggtctta atgttgttaa acttttattt   8640
ttactttata tggtgtgttg atgtgttatg gttttgacaa cttttttttt ttctggattt   8700
ttgcagattt aaggaagcca tggcccacag caagcacggc ctgaaggagg agatgaccat   8760
gaagtaccac atggagggct gcgtgaacgg ccacaagttc gtgatcaccg gcgagggcat   8820
cggctacccc ttcaagggca agcagaccat caacctgtgc gtgatcgagg gcggcccccct  8880
gcccttcagc gaggacatcc tgagcgccgg cttcaagtac ggcgaccgga tcttcaccga   8940
gtacccccag gacatcgtgg actacttcaa gaacagctgc cccgccggct acacctgggg   9000
ccggagcttc ctgttcgagg acggcgccgt gtgcatctgt aacgtggaca tcaccgtgag   9060
cgtgaaggag aactgcatct accacaagag catcttcaac ggcgtgaact tccccgccga   9120
cggccccgtg atgaagaaga tgaccaccaa ctgggaggcc agctgcgaga agatcatgcc   9180
cgtgcctaag cagggcatcc tgaagggcga cgtgagcatg tacctgctgc tgaaggacgg   9240
cggccggtac cggtgccagt tcgacaccgt gtacaaggcc aagagcgtgc ccagcaagat   9300
gcccgagtgg cacttcatcc agcacaagct gctgcgggag gaccggagcg acgccaagaa   9360
ccagaagtgg cagctgaccg agcacgccat cgccttcccc agcgccctgg cctgagagct   9420
```

-continued cgaatttccc cgatcgttca aacatttggc aataaagttt cttaagattg aatcctgttg 9480
ccggtcttgc gatgattatc atataatttc tgttgaatta cgttaagcat gtaataatta 9540
acatgtaatg catgacgtta tttatgagat gggtttttat gattagagtc ccgcaattat 9600
acatttaata cgcgatagaa aacaaaatat agcgcgcaaa ctaggataaa ttatcgcgcg 9660
cggtgtcatc tatgttacta gatcgggaat tctagtggcc ggcccagctg atatccatca 9720
cactggcggc cgcactcgac tgaattggtt ccggcgccag cctgcttt 9768

<210> SEQ ID NO 25
<211> LENGTH: 5839
<212> TYPE: DNA
<213> ORGANISM: artificial
<220> FEATURE:
<223> OTHER INFORMATION: vector

<400> SEQUENCE: 25
cttgtacaaa gtggttgatg ggatccatgg cccacagcaa gcacggcctg aaggaggaga 60
tgaccatgaa gtaccacatg gagggctgcg tgaacggcca caagttcgtg atcaccggcg 120
agggcatcgg ctaccccttc aagggcaagc agaccatcaa cctgtgcgtg atcgagggcg 180 gcccccctgcc cttcagcgag gacatcctga gcgccggctt caagtacggc gaccggatct 240
tcaccgagta cccccaggac atcgtggact acttcaagaa cagctgcccc gccggctaca 300
cctggggccg gagcttcctg ttcgaggacg gcgccgtgtg catctgtaac gtggacatca 360
ccgtgagcgt gaaggagaac tgcatctacc acaagagcat cttcaacggc gtgaacttcc 420
ccgccgacgg ccccgtgatg aagaagatga ccaccaactg ggaggccagc tgcgagaaga 480
tcatgcccgt gcctaagcag ggcatcctga agggcgacgt gagcatgtac ctgctgctga 540
aggacggcgg ccggtaccgg tgccagttcg acaccgtgta caaggccaag agcgtgccca 600
gcaagatgcc cgagtggcac ttcatccagc acaagctgct gcgggaggac cggagcgacg 660
ccaagaacca gaagtggcag ctgaccgagc acgccatcgc cttccccagc gccctggcct 720
gagagctcga atttccccga tcgttcaaac atttggcaat aaagtttctt aagattgaat 780
cctgttgccg gtcttgcgat gattatcata taatttctgt tgaattacgt taagcatgta 840
ataattaaca tgtaatgcat gacgttattt atgagatggg tttttatgat tagagtcccg 900
caattataca tttaatacgc gatagaaaac aaaatatagc gcgcaaacta ggataaatta 960
tcgcgcgcgg tgtcatctat gttactagat cgggaattct agtggccggc ccagctgata 1020
tccatcacac tggcggccgc tcgagttcta tagtgtcacc taaatcgtat gtgtatgata 1080
cataaggtta tgtattaatt gtagccgcgt tctaacgaca atatgtccat atggtgcact 1140
ctcagtacaa tctgctctga tgccgcatag ttaagccagc cccgacaccc gccaacaccc 1200
gctgacgcgc cctgacgggc ttgtctgctc ccggcatccg cttacagaca agctgtgacc 1260
gtctccggga gctgcatgtg tcagaggttt tcaccgtcat caccgaaacg cgcgagacga 1320
aagggcctcg tgatacgcct atttttatag gttaatgtca tgaccaaaat cccttaacgt 1380
gagttttcgt tccactgagc gtcagacccc gtagaaaaga tcaaaggatc ttcttgagat 1440
cctttttttc tgcgcgtaat ctgctgcttg caaacaaaaa aaccaccgct accagcggtg 1500
gtttgtttgc cggatcaaga gctaccaact ctttttccga aggtaactgg cttcagcaga 1560
gcgcagatac caaatactgt ccttctagtg tagccgtagt taggccacca cttcaagaac 1620
tctgtagcac cgcctacata cctcgctctg ctaatcctgt taccagtggc tgctgccagt 1680
ggcgataagt cgtgtcttac cgggttggac tcaagacgat agttaccgga taaggcgcag 1740

-continued

```
cggtcgggct gaacgggggg ttcgtgcaca cagcccagct tggagcgaac gacctacacc   1800

gaactgagat acctacagcg tgagcattga gaaagcgcca cgcttcccga agggagaaag   1860

gcggacaggt atccggtaag cggcagggtc ggaacaggag agcgcacgag ggagcttcca   1920

gggggaaacg cctggtatct ttatagtcct gtcgggtttc gccacctctg acttgagcgt   1980

cgatttttgt gatgctcgtc aggggggcgg agcctatgga aaaacgccag caacgcggcc   2040

tttttacggt tcctggcctt ttgctggcct tttgctcaca tgttctttcc tgcgttatcc   2100

cctgattctg tggataaccg tattaccgcc tttgagtgag ctgataccgc tcgccgcagc   2160

cgaacgaccg agcgcagcga gtcagtgagc gaggaagcgg aagagcgccc aatacgcaaa   2220

ccgcctctcc ccgcgcgttg gccgattcat taatgcaggt tgatcagatc tcgatcccgc   2280

gaaattaata cgactcacta tagggagacc acaacggttt ccctctagaa ataattttgt   2340

ttaactttaa gaaggagata tacccatgga aaagcctgaa ctcaccgcga cgtctgtcga   2400

gaagtttctg atcgaaaagt tcgacagcgt ctccgacctg atgcagctct cggagggcga   2460

agaatctcgt gctttcagct tcgatgtagg agggcgtgga tatgtcctgc gggtaaatag   2520

ctgcgccgat ggtttctaca aagatcgtta tgtttatcgg cactttgcat cggccgcgct   2580

cccgattccg gaagtgcttg acattgggga attcagcgag agcctgacct attgcatctc   2640

ccgccgtgca cagggtgtca cgttgcaaga cctgcctgaa accgaactgc ccgctgttct   2700

gcagccggtc gcggaggcta tggatgcgat cgctgcggcc gatcttagcc agacgagcgg   2760

gttcggccca ttcggaccgc aaggaatcgg tcaatacact acatggcgtg atttcatatg   2820

cgcgattgct gatccccatg tgtatcactg gcaaactgtg atggacgaca ccgtcagtgc   2880

gtccgtcgcg caggctctcg atgagctgat gctttgggcc gaggactgcc ccgaagtccg   2940

gcacctcgtg cacgcggatt tcggctccaa caatgtcctg acggacaatg gccgcataac   3000

agcggtcatt gactggagcg aggcgatgtt cggggattcc caatacgagg tcgccaacat   3060

cttcttctgg aggccgtggt tggcttgtat ggagcagcag acgcgctact tcgagcggag   3120

gcatccggag cttgcaggat cgccgcggct ccgggcgtat atgctccgca ttggtcttga   3180

ccaactctat cagagcttgg ttgacggcaa tttcgatgat gcagcttggg cgcagggtcg   3240

atgcgacgca atcgtccgat ccggagccgg gactgtcggg cgtacacaaa tcgcccgcag   3300

aagcgcggcc gtctggaccg atggctgtgt agaagtactc gccgatagtg gaaaccgacg   3360

ccccagcact cgtccgaggg caaaggaata gtgaggtaca gcttggatcg atccggctgc   3420

taacaaagcc cgaaaggaag ctgagttggc tgctgccacc gctgagcaat aactagcata   3480

accccttggg gcctctaaac gggtcttgag gggttttttg ctgaaaggag gaactatatc   3540

cggatgatcg tcgaggcctc acgtgttaac aagcttgcat gcctgcaggt ttatcaacaa   3600

gtttgtacaa aaaagcaggc tccgaattcg cccttgggca atcaaattat atatgtaaag   3660

caattacagt ttatcaaact ttatttatgg aaataattta ttatcacatt tattttggtt   3720

tataaatttt aaattaaaat atcacctaaa taaaaataat ttttaacatg acttattgtc   3780

ctaaataaat tatttccgta aattaaataa aatgaagttt ttttctttca aagaatctaa   3840

atggtcataa tgagaattct ctaaaaaaat acataatgag aataattatg gaatttattt   3900

attaataaaa attaatagca ttttgataga caattaataa aattttaaaa ataaccatat   3960

agaaataata atttttttac tatcggttcc aattaaaata atgataaaaa ataaaataga   4020

ttattaattg atattgatat gaaatttaaa taaagaatat aatcatatat tttattgata   4080

tatgatatga tatagattaa ttgatattga ttttgatatg gaatttaaaa ataatataat   4140
```

-continued aattgttttt atttattaat acgtgtaatc aaataattct cactttttga atcaatcagt 4200
gtacttaaag ataatatcag ttgaatattt tttatccttt tacgtgtgct gtgagacatt 4260
atcatcaatt gtgttgtata tgatatatag atatagatat ataaatatat agattgagtg 4320
atataatata tttaaaatat aaattatata tatgttttaa tatatttttg catatatata 4380
tatatttgta aaaactagaa gtatttttca tgagataatt attatcgagt tgaataagtc 4440
tattatttgt gagagccaac catatttata tatgtgatta aattttatct ttgtgaaatt 4500
aaaaataata aaaaatacct taaaatcata ataatagaaa aacttatatt tataatttac 4560
cattatactt aaaaaaaatt aaataaatat tataaatata aatactatcg agtaatggcc 4620
gcgctagggt ttttgagaaa aaatcttccc acgcactcaa ctgcactgta cggcgtcgtt 4680
ttcacagccg cataatagaa gccgcgttcc ccaacccttc ctcacaacat tctcggaccc 4740
tccagcaccg tcacccaaac aaatatccac gcggtagtag gcgcgtgaaa caaactctaa 4800
tccgaactac gagacgtgag aagcacgcgc tttagcgagc gtttcaattg tcgctacgaa 4860
agcagagaag gatacaaacg gaactagggt aaattagtaa gggtaatttc gtaaacagaa 4920
gaaaagagtt gtagctataa ataaaccctc taaccctcgt cgcattactt ctcttcacac 4980
ctttgttcac tcttcttctc ttgcggctag ggttttagcg cagcttcttc taggttcgtt 5040
atctaccacc gttctatgga ttttattcct tctattcgtg tttattctat tggtttatgt 5100
tgcttgcaat atgtttttc tgaatctgtc gtcgttgtct tcaattttat ccatgtttca 5160
gagatcaatt ttgtttgtgt agtatgtgct tattcttctt cttttcgttc gagttgttaa 5220
taacggtgct atggtgtttt caaaagtgtt ttttttatta cttttgattt aaagtttttt 5280
tggtaaggct tttatttgct tgttatattc aaatctttgg atccagatct tatataagtt 5340
tttggttcaa gaaagttttt ggttactgat gaatagatct attaactgtt actttaatcg 5400
attcaagcta aagtttttg gttactgatg aatagatcta ttatctgtta cttttaatcg 5460
gttcaagctc aagtttttg gttactgatg aatagatcta tatacgtcac agtgtgctaa 5520
acatgccctt gttttatctc gatcttatgt atgggagtgc cataaatttt gttatgtcta 5580
tttttttatc tgttggaatc atactgagtt tgatgcgtta cgattgagca tacctatttt 5640
tgggcttgtt gtatggtggg tatttagatc ttaatctttt tatgcttatg aaaggttttg 5700
taatgacaaa ggtcttaatg ttgttaaact tttattttta ctttatatgg tgtgttgatg 5760
tgttatggtt ttgacaactt ttttttttc tggatttttg cagatttaag gaagccaagg 5820
gcgaattcga cccagcttt 5839

<210> SEQ ID NO 26
<211> LENGTH: 26
<212> TYPE: DNA
<213> ORGANISM: artificial
<220> FEATURE:
<223> OTHER INFORMATION: primer

<400> SEQUENCE: 26
gaccaagaca cactcgttca tatatc 26

<210> SEQ ID NO 27
<211> LENGTH: 25
<212> TYPE: DNA
<213> ORGANISM: artificial
<220> FEATURE:
<223> OTHER INFORMATION: primer

<400> SEQUENCE: 27

-continued tctgctgctc aatgtttaca aggac 25

<210> SEQ ID NO 28
<211> LENGTH: 22
<212> TYPE: DNA
<213> ORGANISM: artificial
<220> FEATURE:
<223> OTHER INFORMATION: primer

<400> SEQUENCE: 28
ggaagaagag aatcgggtgg tt 22

<210> SEQ ID NO 29
<211> LENGTH: 23
<212> TYPE: DNA
<213> ORGANISM: artificial
<220> FEATURE:
<223> OTHER INFORMATION: oligo probe

<400> SEQUENCE: 29
attgtgttgt gtggcatggt tat 23

<210> SEQ ID NO 30
<211> LENGTH: 23
<212> TYPE: DNA
<213> ORGANISM: artificial
<220> FEATURE:
<223> OTHER INFORMATION: primer

<400> SEQUENCE: 30
ggcttgttgt gcagtttttg aag 23

<210> SEQ ID NO 31
<211> LENGTH: 20
<212> TYPE: DNA
<213> ORGANISM: artificial
<220> FEATURE:
<223> OTHER INFORMATION: primer

<400> SEQUENCE: 31
aacggccaca agttcgtgat 20

<210> SEQ ID NO 32
<211> LENGTH: 20
<212> TYPE: DNA
<213> ORGANISM: artificial
<220> FEATURE:
<223> OTHER INFORMATION: oligo probe

<400> SEQUENCE: 32
accggcgagg gcatcggcta 20

<210> SEQ ID NO 33
<211> LENGTH: 20
<212> TYPE: DNA
<213> ORGANISM: artificial
<220> FEATURE:
<223> OTHER INFORMATION: primer

<400> SEQUENCE: 33
cttcaagggc aagcagacca 20

<210> SEQ ID NO 34
<211> LENGTH: 24
<212> TYPE: DNA
<213> ORGANISM: artificial
<220> FEATURE:

<223> OTHER INFORMATION: primer

<400> SEQUENCE: 34
caaacttgac aaagccacaa ctct 24

<210> SEQ ID NO 35
<211> LENGTH: 20
<212> TYPE: DNA
<213> ORGANISM: artificial
<220> FEATURE:
<223> OTHER INFORMATION: oligo probe

<400> SEQUENCE: 35
ctctcatctc atataaatac 20

<210> SEQ ID NO 36
<211> LENGTH: 21
<212> TYPE: DNA
<213> ORGANISM: artificial
<220> FEATURE:
<223> OTHER INFORMATION: primer

<400> SEQUENCE: 36
ggagaaattg gtgtcgtgga a 21

<210> SEQ ID NO 37
<211> LENGTH: 100
<212> TYPE: DNA
<213> ORGANISM: artificial
<220> FEATURE:
<223> OTHER INFORMATION: attL1 recombination site

<400> SEQUENCE: 37
caaataatga ttttattttg actgatagtg acctgttcgt tgcaacaaat tgataagcaa 60
tgctttttta taatgccaac tttgtacaaa aaagcaggct 100

<210> SEQ ID NO 38
<211> LENGTH: 100
<212> TYPE: DNA
<213> ORGANISM: artificial
<220> FEATURE:
<223> OTHER INFORMATION: attL2 recombination site

<400> SEQUENCE: 38
caaataatga ttttattttg actgatagtg acctgttcgt tgcaacaaat tgataagcaa 60
tgctttctta taatgccaac tttgtacaag aaagctgggt 100

<210> SEQ ID NO 39
<211> LENGTH: 125
<212> TYPE: DNA
<213> ORGANISM: artificial
<220> FEATURE:
<223> OTHER INFORMATION: attR1 recombination site

<400> SEQUENCE: 39
acaagtttgt acaaaaaagc tgaacgagaa acgtaaaatg atataaatat caatatatta 60
aattagattt tgcataaaaa acagactaca taatactgta aaacacaaca tatccagtca 120
ctatg 125

<210> SEQ ID NO 40
<211> LENGTH: 125
<212> TYPE: DNA
<213> ORGANISM: artificial
<220> FEATURE:

-continued

```
<223> OTHER INFORMATION: attR2 recombiantion site

<400> SEQUENCE: 40

accactttgt acaagaaagc tgaacgagaa acgtaaaatg atataaatat caatatatta     60

aattagattt tgcataaaaa acagactaca taatactgta aaacacaaca tatccagtca    120

ctatg                                                                125


<210> SEQ ID NO 41
<211> LENGTH: 21
<212> TYPE: DNA
<213> ORGANISM: artificial
<220> FEATURE:
<223> OTHER INFORMATION: attB1 recombination site

<400> SEQUENCE: 41

caagtttgta caaaaaagca g                                               21


<210> SEQ ID NO 42
<211> LENGTH: 21
<212> TYPE: DNA
<213> ORGANISM: artificial
<220> FEATURE:
<223> OTHER INFORMATION: attB2 recombiantion site

<400> SEQUENCE: 42

cagctttctt gtacaaagtg g                                               21


<210> SEQ ID NO 43
<211> LENGTH: 17
<212> TYPE: DNA
<213> ORGANISM: artificial
<220> FEATURE:
<223> OTHER INFORMATION: Tag sequence

<400> SEQUENCE: 43

gatcgacggt ggcaaga                                                    17
```

SOYBEAN EF1A PROMOTER AND ITS USE IN CONSTITUTIVE EXPRESSION OF TRANSGENIC GENES IN PLANTS

FIELD OF THE INVENTION

This invention relates to a plant promoter GM-EF1A and fragments thereof and their use in altering expression of at least one heterologous nucleic acid fragment in plants in a tissue-independent or constitutive manner.

BACKGROUND

Recent advances in plant genetic engineering have opened new doors to engineer plants to have improved characteristics or traits, such as plant disease resistance, insect resistance, herbicidal resistance, yield improvement, improvement of the nutritional quality of the edible portions of the plant, and enhanced stability or shelf-life of the ultimate consumer product obtained from the plants. Thus, a desired gene (or genes) with the molecular function to impart different or improved characteristics or qualities, can be incorporated properly into the plant's genome. The newly integrated gene (or genes) coding sequence can then be expressed in the plant cell to exhibit the desired new trait or characteristics. It is important that appropriate regulatory signals must be present in proper configurations in order to obtain the expression of the newly inserted gene coding sequence in the plant cell. These regulatory signals typically include a promoter region, a 5' non-translated leader sequence and a 3' transcription termination/polyadenylation sequence.

A promoter is a non-coding genomic DNA sequence, usually upstream (5') to the relevant coding sequence, to which RNA polymerase binds before initiating transcription. This binding aligns the RNA polymerase so that transcription will initiate at a specific transcription initiation site. The nucleotide sequence of the promoter determines the nature of the enzyme and other related protein factors that attach to it and the rate of RNA synthesis. The RNA is processed to produce messenger RNA (mRNA) which serves as a template for translation of the RNA sequence into the amino acid sequence of the encoded polypeptide. The 5' non-translated leader sequence is a region of the mRNA upstream of the coding region that may play a role in initiation and translation of the mRNA. The 3' transcription termination/polyadenylation signal is a non-translated region downstream of the coding region that functions in the plant cell to cause termination of the RNA synthesis and the addition of polyadenylate nucleotides to the 3' end.

It has been shown that certain promoters are able to direct RNA synthesis at a higher rate than others. These are called "strong promoters". Certain other promoters have been shown to direct RNA synthesis at higher levels only in particular types of cells or tissues and are often referred to as "tissue specific promoters", or "tissue-preferred promoters" if the promoters direct RNA synthesis preferably in certain tissues but also in other tissues at reduced levels. Since the patterns of the expression of a chimeric gene (or genes) introduced into a plant are controlled using promoters, there is an ongoing interest in the isolation of novel promoters which are capable of controlling the expression of a chimeric gene or (genes) at certain levels in specific tissue types or at specific plant developmental stages.

Certain promoters are able to direct RNA synthesis at relatively similar levels across all tissues of a plant. These are called "constitutive promoters" or "tissue-independent" promoters. Constitutive promoters can be divided into strong, moderate and weak according to their effectiveness to direct RNA synthesis. Since it is necessary in many cases to simultaneously express a chimeric gene (or genes) in different tissues of a plant to get the desired functions of the gene (or genes), constitutive promoters are especially useful in this consideration. Though many constitutive promoters have been discovered from plants and plant viruses and characterized, there is still an ongoing interest in the isolation of more novel constitutive promoters which are capable of controlling the expression of a chimeric gene or (genes) at different levels and the expression of multiple genes in the same transgenic plant for gene stacking.

SUMMARY OF THE INVENTION

This invention concerns an isolated nucleic acid fragment comprising a promoter wherein said promoter consists essentially of the nucleotide sequence set forth in SEQ ID NOs: 1, 2, 3, 4, 5, 6, 7 or said promoter consists essentially of a fragment that is substantially similar and functionally equivalent to the nucleotide sequence set forth in SEQ ID NOs: 1, 2, 3, 4, 5, 6, 7.

In a second embodiment, this invention concerns a recombinant expression construct comprising at least one heterologous nucleic acid fragment operably linked to the promoter of the invention.

In a third embodiment, this invention concerns a cell, plant, or seed comprising a recombinant expression construct of the present disclosure.

In a fourth embodiment, this invention concerns plants comprising this recombinant expression construct and seeds obtained from such plants.

In a fifth embodiment, this invention concerns a method of altering (increasing or decreasing) expression of at least one heterologous nucleic acid fragment in a plant cell which comprises:

(a) transforming a plant cell with the recombinant expression construct described above;
(b) growing fertile mature plants from the transformed plant cell of step (a);
(c) selecting plants containing the transformed plant cell wherein the expression of the heterologous nucleic acid fragment is increased or decreased.

In a sixth embodiment, this invention concerns a method for expressing a yellow fluorescent protein ZS-YELLOW1 N1 in a host cell comprising:

(a) transforming a host cell with a recombinant expression construct comprising at least one ZS-YELLOW1 N1 (YFP) nucleic acid fragment operably linked to a promoter wherein said promoter consists essentially of the nucleotide sequence set forth in SEQ ID NOs:1, 2, 3, 4, 5, 6, or 7; and
(b) growing the transformed host cell under conditions that are suitable for expression of the recombinant DNA construct, wherein expression of the recombinant DNA construct results in production of increased levels of ZS-YELLOW1 N1 protein in the transformed host cell when compared to a corresponding nontransformed host cell.

In a seventh embodiment, this invention concerns an isolated nucleic acid fragment comprising a plant translation elongation factor EF1A gene promoter.

In an eighth embodiment, this invention concerns a method of altering a marketable plant trait. The marketable plant trait concerns genes and proteins involved in disease resistance, herbicide resistance, insect resistance, carbohydrate metabolism, fatty acid metabolism, amino acid metabolism, plant development, plant growth regulation, yield improvement, drought resistance, cold resistance, heat resistance, and salt resistance.

In a ninth embodiment, this invention concerns an isolated polynucleotide linked to a heterologous nucleic acid sequence. The heterologous nucleic acid sequence encodes a protein involved in disease resistance, herbicide resistance, insect resistance; carbohydrate metabolism, fatty acid metabolism, amino acid metabolism, plant development, plant growth regulation, yield improvement, drought resistance, cold resistance, heat resistance, or salt resistance in plants.

BRIEF DESCRIPTION OF THE DRAWINGS AND SEQUENCES

The invention can be more fully understood from the following detailed descriptions, the drawings and the sequence descriptions that form a part of this application. The sequence descriptions and sequence listing attached hereto comply with the rules governing nucleotide and/or amino acid sequence disclosures in patent applications as set forth in 37 C.F.R. §1.821-1.825. The sequence descriptions contain the three letter codes for amino acids as defined in 37 C.F.R. §1.821-1.825, which are incorporated herein by reference.

SEQ ID NO:1 is the DNA sequence comprising a 2181 bp (base pair) soybean EF1A promoter.

SEQ ID NO:2 is a 1841 bp truncated form of the EF1A promoter shown in SEQ ID NO:1 (bp 340-2181 of SEQ ID NO:1).

SEQ ID NO:3 is a 1642 bp truncated form of the EF1A promoter shown in SEQ ID NO:1 (bp 539-2181 of SEQ ID NO:1).

SEQ ID NO:4 is a 1431 bp truncated form of the EF1A promoter shown in SEQ ID NO:1 (bp 750-2181 of SEQ ID NO:1).

SEQ ID NO:5 is a 1215 bp truncated form of the EF1A promoter shown in SEQ ID NO:1 (bp 966-2181 of SEQ ID NO:1).

SEQ ID NO:6 is a 1012 bp truncated form of the EF1A promoter shown in SEQ ID NO:1 (bp 1169-2181 of SEQ ID NO:1).

SEQ ID NO:7 is a 837 bp truncated form of the EF1A promoter shown in SEQ ID NO:1 (bp 1344-2181 of SEQ ID NO:1).

SEQ ID NO:8 is an oligonucleotide primer used as an antisense primer in the PCR amplifications of the full length EF1A promoter in SEQ ID NO:1 when paired with SEQ ID NO:9, and the truncated EF1A promoters in SEQ ID NOs:2, 3, 4, 5, 6, or 7 when paired with SEQ ID NOs:10, 11, 12, 13, 14 or 15, respectively.

SEQ ID NO:9 is an oligonucleotide primer used as a sense primer in the PCR amplification of the full length EF1A promoter in SEQ ID NO:1 when paired with SEQ ID NO:8.

SEQ ID NO:10 is an oligonucleotide primer used as a sense primer in the PCR amplification of the truncated EF1A promoter in SEQ ID NO:2 when paired with SEQ ID NO:8.

SEQ ID NO:11 is an oligonucleotide primer used as a sense primer in the PCR amplification of the truncated EF1A promoter in SEQ ID NO:3 when paired with SEQ ID NO:8.

SEQ ID NO:12 is an oligonucleotide primer used as a sense primer in the PCR amplification of the truncated EF1A promoter in SEQ ID NO:4 when paired with SEQ ID NO:8.

SEQ ID NO:13 is an oligonucleotide primer used as a sense primer in the PCR amplification of the truncated EF1A promoter in SEQ ID NO:5 when paired with SEQ ID NO:8.

SEQ ID NO:14 is an oligonucleotide primer used as a sense primer in the PCR amplification of the truncated EF1A promoter in SEQ ID NO:6 when paired with SEQ ID NO:8.

SEQ ID NO:15 is an oligonucleotide primer used as a sense primer in the PCR amplification of the truncated EF1A promoter in SEQ ID NO:7 when paired with SEQ ID NO:8

SEQ ID NO:16 is a 770 bp intron located in the 5' untranslated region (5UTR) of the EF1A gene as revealed by sequence alignment between the EF1A promoter and EF1A cDNA sequence.

SEQ ID NO:17 is a 54 bp putative 5' untranslated region (5UTR) upstream of the 770 bp intron SEQ ID NO:16 of the EF1A gene.

SEQ ID NO:18 is a 13 bp putative 5' untranslated region (5UTR) downstream of the 770 bp intron SEQ ID NO:16 of the EF1A gene. The last two base pairs CC are not naturally present in the EF1A gene and are extra base pairs introduced as part of the NcoI cloning site CCATGG.

SEQ ID NO:19 is a 41 bp oligonucleotide primer specific to the soybean EF1A promoter 5' end for the amplification of the promoter when paired with SEQ ID NO:20. A XmaI restriction site CCCGGG is added for subsequent cloning.

SEQ ID NO:20 is a 35 bp oligonucleotide primer specific to the soybean EF1A promoter 3' end for the amplification of the promoter when paired with SEQ ID NO:19. A NcoI restriction site CCATGG is added for subsequent cloning.

SEQ ID NO:21 is the 1724 bp nucleotide sequence of the putative soybean translation elongation factor EF1A gene. Nucleotides 1 to 65 are the 5' untranslated sequence, nucleotides 66 to 68 are the translation initiation codon, nucleotides 66 to 1406 are the polypeptide coding region, nucleotides 1407 to 1409 are the termination codon, and nucleotides 1410 to 1724 are part of the 3' untranslated sequence.

SEQ ID NO:22 is the predicted 447 aa (amino acid) long protein sequence translated from the coding region of the putative soybean translation elongation factor EF1A gene nucleotide sequence SEQ ID NO:21.

SEQ ID NO:23 is the 5465 bp sequence of QC314.

SEQ ID NO:24 is the 9768 bp sequence of QC318.

SEQ ID NO:25 is the 5839 bp sequence of QC314-1Y.

SEQ ID NO:26 is an oligonucleotide primer used in the diagnostic PCR to check for soybean genomic DNA presence in total RNA or cDNA when paired with SEQ ID NO:27.

SEQ ID NO:27 is an oligonucleotide primer used in the diagnostic PCR to check for soybean genomic DNA presence in total RNA or cDNA when paired with SEQ ID NO:26.

SEQ ID NO:28 is a sense primer used in quantitative PCR analysis of SAMS:ALS transgene copy numbers.

SEQ ID NO:29 is a FAM labeled fluorescent DNA oligo probe used in quantitative PCR analysis of SAMS:ALS transgene copy numbers.

SEQ ID NO:30 is an antisense primer used in quantitative PCR analysis of SAMS:ALS transgene copy numbers.

SEQ ID NO:31 is a sense primer used in quantitative PCR analysis of GM-EFA1:YFP transgene copy numbers.

SEQ ID NO:32 is a FAM labeled fluorescent DNA oligo probe used in quantitative PCR analysis of GM-EFA1:YFP transgene copy numbers.

SEQ ID NO:33 is an antisense primer used in quantitative PCR analysis of GM-EFA1:YFP transgene copy numbers.

SEQ ID NO:34 is a sense primer used as an endogenous control gene primer in quantitative PCR analysis of transgene copy numbers.

SEQ ID NO:35 is a VIC labeled DNA oligo probe used as an endogenous control gene probe in quantitative PCR analysis of transgene copy numbers.

SEQ ID NO:36 is an antisense primer used as an endogenous control gene primer in quantitative PCR analysis of transgene copy numbers.

SEQ ID NO:37 is the recombination site attL1 sequence in the Gateway cloning system (Invitrogen).

SEQ ID NO:38 is the recombination site attL2 sequence in the Gateway cloning system (Invitrogen).

SEQ ID NO:39 is the recombination site attR1 sequence in the Gateway cloning system (Invitrogen).

SEQ ID NO:40 is the recombination site attR2 sequence in the Gateway cloning system (Invitrogen).

SEQ ID NO:41 is the recombination site attB1 sequence in the Gateway cloning system (Invitrogen).

SEQ ID NO:42 is the recombination site attB2 sequence in the Gateway cloning system (Invitrogen).

SEQ ID NO:43 is the 17 base signature tag used in the MPSS analysis described in Example 1.

Figure 5:
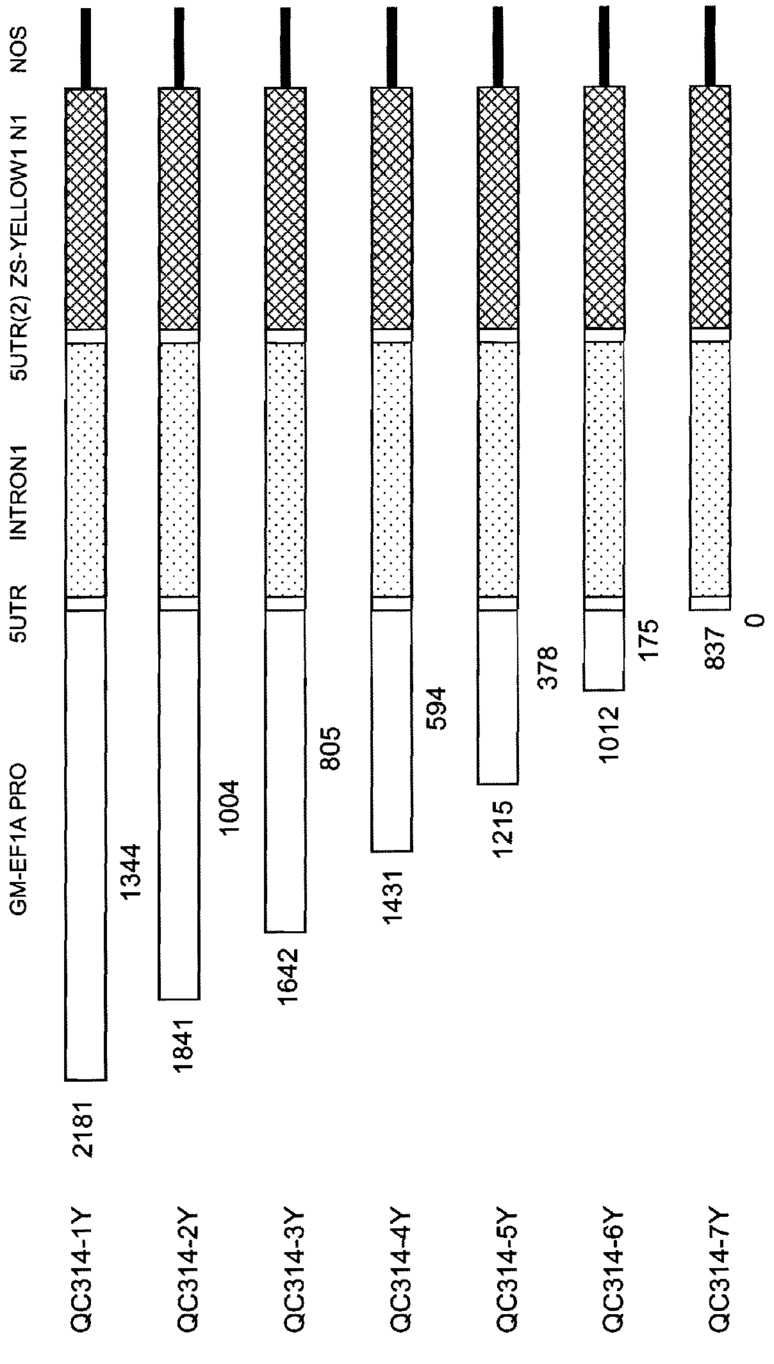

FIG. 5 is the schematic description of the progressive truncation constructs, QC314-1Y, QC314-2Y, QC314-3Y, QC314-4Y, QC314-5Y, QC314-6Y, and QC314-7Y, of the EF1A promoter. The size of each promoter deletion including the 5'UTR, 5'UTR intron is given at the left end of each drawing. The size of the promoter region upstream of the 5'UTR is given under each drawing.

Figure 6:
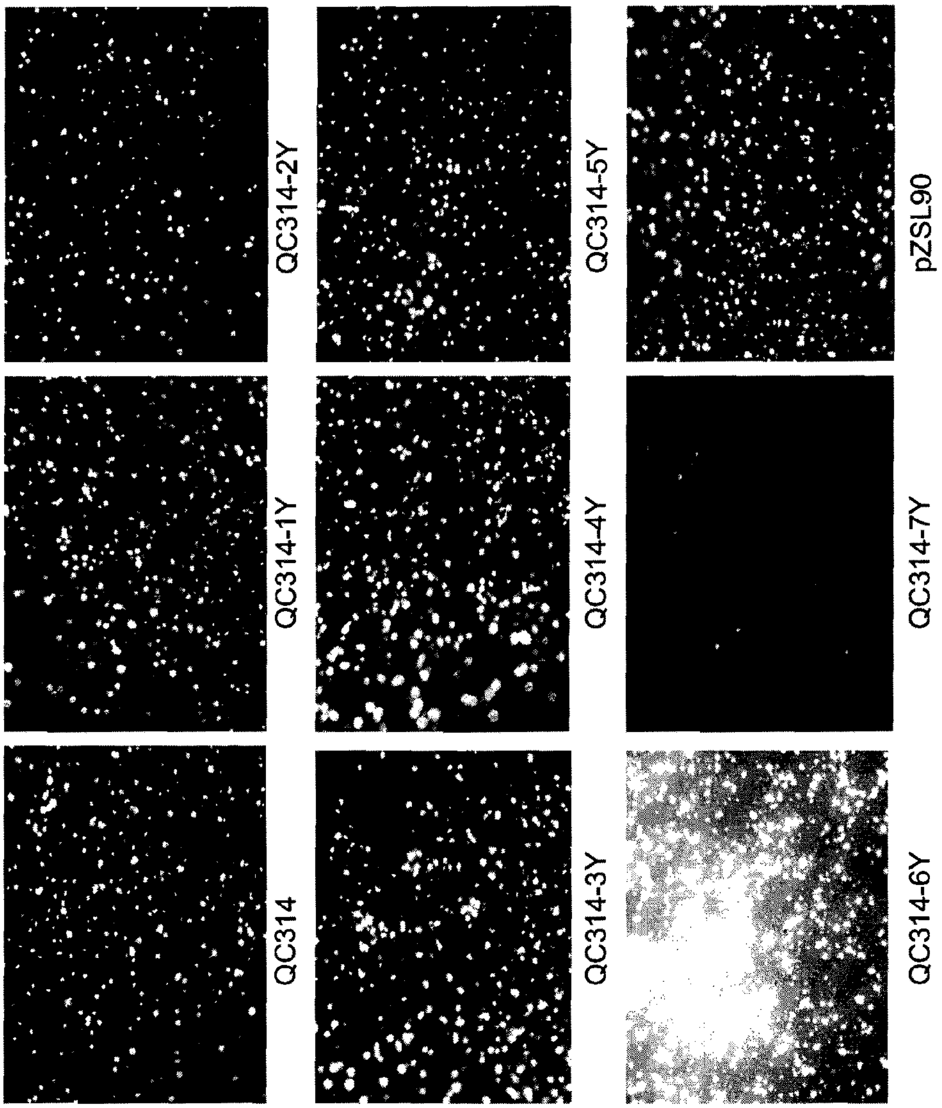

FIG. 6 is the transient expression of the fluorescent protein reporter gene ZS-YELLOW1 N1 in the cotyledons of germinating soybean seeds. The reporter gene is driven by the full length EF1A promoter in QC314 or by progressively truncated EF1A promoters in the transient expression constructs QC314-1Y to QC314-7Y.

Figure 7:
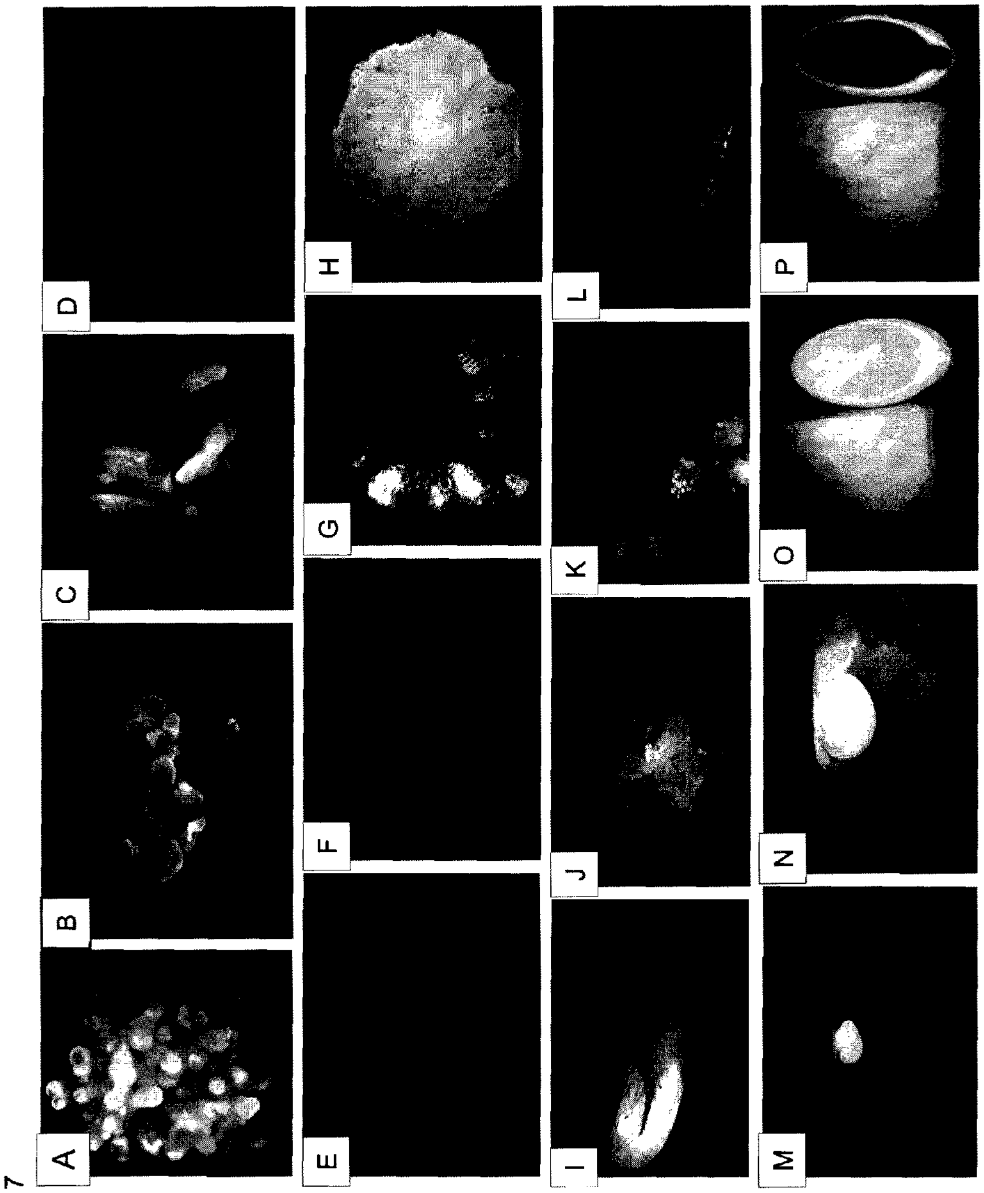

FIG. 7 is the stable expression of the fluorescent protein reporter gene ZS-YELLOW1 N1 in transgenic soybean plants containing a single copy of the transgene construct QC318.

DETAILED DESCRIPTION OF THE INVENTION

The disclosure of all patents, patent applications, and publications cited herein are incorporated by reference in their entirety.

In the context of this disclosure, a number of terms shall be utilized.

As used herein, a "GM-EF1A promoter" refers to a promoter of the *Glycine max* EF-1-alpha polypeptide which is a putative soybean protein with significant homology to translation elongation factor EF-1$\alpha$ genes identified in various species including soybean (Aguilar et al, Plant Mol. Biol. 17 (3), 351-360 (1991)).

The term "constitutive promoter" refers to promoters active in all or most tissues of a plant at all or most developing stages. As with other promoters classified as "constitutive" (e.g. ubiquitin), some variation in absolute levels of expression can exist among different tissues or stages.

The term "constitutive promoter" or "tissue-independent" are used interchangeably herewithin.

The promoter nucleotide sequences and methods disclosed herein are useful in regulating constitutive expression of any heterologous nucleotide sequences in a host plant in order to alter the phenotype of a plant.

Various changes in phenotype are of interest including, but not limited to, modifying the fatty acid composition in a plant, altering the amino acid content of a plant, altering a plant's pathogen defense mechanism, and the like. These results can be achieved by providing expression of heterologous products or increased expression of endogenous products in plants. Alternatively, the results can be achieved by providing for a reduction of expression of one or more endogenous products, particularly enzymes or cofactors in the plant. These changes result in a change in phenotype of the transformed plant.

Genes of interest are reflective of the commercial markets and interests of those involved in the development of the crop. Crops and markets of interest change, and as developing nations open up world markets, new crops and technologies will emerge also. In addition, as our understanding of agronomic characteristics and traits such as yield and heterosis increase, the choice of genes for transformation will change accordingly. General categories of genes of interest include, but are not limited to, those genes involved in information, such as zinc fingers, those involved in communication, such as kinases, and those involved in housekeeping, such as heat shock proteins. More specific categories of transgenes, for example, include, but are not limited to, genes encoding important traits for agronomics, insect resistance, disease resistance, herbicide resistance, sterility, grain or seed characteristics, and commercial products. Genes of interest include, generally, those involved in oil, starch, carbohydrate, or nutrient metabolism as well as those affecting seed size, plant development, plant growth regulation, and yield improvement. Plant development and growth regulation also refer to the development and growth regulation of various parts of a plant, such as the flower, seed, root, leaf and shoot.

Other commercially desirable traits are genes and proteins conferring cold, heat, salt, and drought resistance.

Disease and/or insect resistance genes may encode resistance to pests that have great yield drag such as for example, Anthracnose, Soybean Mosaic Virus, Soybean Cyst Nematode, Root-Knot Nematode, Brown leaf spot, Downy Mildew, Purple Seed Stain, Seed Decay and Seedling Diseases caused commonly by the fungi—*Pythium* sp., *Phytophthora* sp., *Rhizoctonia* sp., *Diaporthe* sp. Bacterial Blight caused by the bacterium *Pseudomonas syringae* pv. *Glycinea*. Genes conferring insect resistance include, for example, *Bacillus thuringiensis* toxic protein genes (U.S. Pat. Nos. 5,366,892; 5,747,450; 5,737,514; 5,723,756; 5,593,881; and Geiser et al (1986) Gene 48:109); lectins (Van Damme et al. (1994) Plant Mol. Biol. 24:825); and the like.

Herbicide resistance traits may include genes coding for resistance to herbicides that act to inhibit the action of acetolactate synthase (ALS), in particular the sulfonylurea-type herbicides (e.g., the acetolactate synthase ALS gene containing mutations leading to such resistance, in particular the S4 and/or Hra mutations). The ALS-gene mutants encode resistance to the herbicide chlorosulfuron. GAT is an N-acetyltransferase from *Bacillus licheniformis* that was optimized by gene shuffling for acetylation of the broad spectrum herbicide, glyphosate, forming the basis of a novel mechanism of glyphosate tolerance in transgenic plants (Castle et al. (2004) *Science* 304, 1151-1154).

Antibiotic resistance genes include, for example, neomycin phosphotransferase (npt) and hygromycin phosphotransferase (hpt). Two neomycin phosphotransferase genes are used in selection of transformed organisms: the neomycin phosphotransferase I (nptI) gene and the neomycin phosphotransferase II (nptII) gene. The second one is more widely used. It was initially isolated from the transposon Tn5 that was present in the bacterium strain *Escherichia coli* K12. The gene codes for the aminoglycoside 3'-phosphotransferase (denoted aph(3')-II or NPTII) enzyme, which inactivates by phosphorylation a range of aminoglycoside antibiotics such as kanamycin, neomycin, geneticin and paroromycin. NPTII is widely used as a selectable marker for plant transformation. It is also used in gene expression and regulation studies in different organisms in part because N-terminal fusions can be constructed that retain enzyme activity. NPTII protein activity can be detected by enzymatic assay. In other detection methods, the modified substrates—the phosphorylated antibiotics—are detected by thin-layer chromatography, dot-blot analysis or polyacrylamide gel electrophoresis. Plants such as maize, cotton, tobacco, *Arabidopsis*, flax, soybean and many others have been successfully transformed with the nptII gene.

The hygromycin phosphotransferase (denoted hpt, hph or aphIV) gene was originally derived from *Escherichia coli*. The gene codes for hygromycin phosphotransferase (HPT), which detoxifies the aminocyclitol antibiotic hygromycin B. A large number of plants have been transformed with the hpt gene and hygromycin B has proved very effective in the selection of a wide range of plants, including monocotyledonous. Most plants exhibit higher sensitivity to hygromycin B than to kanamycin, for instance cereals. Likewise, the hpt gene is used widely in selection of transformed mammalian cells. The sequence of the hpt gene has been modified for its use in plant transformation. Deletions and substitutions of amino acid residues close to the carboxy (C)-terminus of the enzyme have increased the level of resistance in certain plants, such as tobacco. At the same time, the hydrophilic C-terminus of the enzyme has been maintained and may be essential for the strong activity of HPT. HPT activity can be checked using an enzymatic assay. A non-destructive callus induction test can be used to verify hygromycin resistance.

Genes involved in plant growth and development have been identified in plants. One such gene, which is involved in cytokinin biosynthesis, is isopentenyl transferase (IPT). Cytokinin plays a critical role in plant growth and development by stimulating cell division and cell differentiation (Sun et al. (2003), Plant Physiol. 131: 167-176).

Calcium-dependent protein kinases (CDPK), a family of serine-threonine kinase found primarily in the plant kingdom, are likely to function as sensor molecules in calcium-mediated signaling pathways. Calcium ions are important second messengers during plant growth and development (Harper et al. Science 252, 951-954 (1993). Roberts et al. Curr Opin Cell Biol 5, 242-246 (1993). Roberts et al. Annu Rev Plant Mol Biol 43, 375-414 (1992)).

Nematode responsive protein (NRP) is produced by soybean upon the infection of soybean cyst nematode. NRP has homology to a taste-modifying glycoprotein miraculin and the NF34 protein involved in tumor formation and hyper response induction. NRP is believed to function as a defense-inducer in response to nematode infection (Tenhaken et al. BMC Bioinformatics 6:169 (2005)).

The quality of seeds and grains is reflected in traits such as levels and types of fatty acids or oils, saturated and unsaturated, quality and quantity of essential amino acids, and levels of carbohydrates. Therefore, commercial traits can also be encoded on a gene or genes that could increase for example methionine and cysteine, two sulfur containing amino acids that are present in low amounts in soybeans. Cystathionine gamma synthase (CGS) and serine acetyl transferase (SAT) are proteins involved in the synthesis of methionine and cysteine, respectively.

Other commercial traits can encode genes to increase for example monounsaturated fatty acids, such as oleic acid, in oil seeds. Soybean oil for example contains high levels of polyunsaturated fatty acids and is more prone to oxidation than oils with higher levels of monounsaturated and saturated fatty acids. High oleic soybean seeds can be prepared by recombinant manipulation of the activity of oleoyl 12-desaturase (Fad2). High oleic soybean oil can be used in applications that require a high degree of oxidative stability, such as cooking for a long period of time at an elevated temperature.

Raffinose saccharides accumulate in significant quantities in the edible portion of many economically significant crop species, such as soybean (*Glycine max* L. Merrill), sugar beet (*Beta vulgaris*), cotton (*Gossypium hirsutum* L.), canola (*Brassica* sp.) and all of the major edible leguminous crops including beans (*Phaseolus* sp.), chick pea (*Cicer arietinum*), cowpea (*Vigna unguiculata*), mung bean (*Vigna radiata*), peas (*Pisum sativum*), lentil (*Lens culinaris*) and lupine (*Lupinus* sp.). Although abundant in many species, raffinose saccharides are an obstacle to the efficient utilization of some economically important crop species.

Downregulation of the expression of the enzymes involved in raffinose saccharide synthesis, such as galactinol synthase for example, would be a desirable trait.

In certain embodiments, the present invention contemplates the transformation of a recipient cell with more than one advantageous transgene. Two or more transgenes can be supplied in a single transformation event using either distinct transgene-encoding vectors, or using a single vector incorporating two or more gene coding sequences. Any two or more transgenes of any description, such as those conferring herbicide, insect, disease (viral, bacterial, fungal, nematode) or drought resistance, oil quantity and quality, or those increasing yield or nutritional quality may be employed as desired.

An "isolated nucleic acid fragment" refers to a polymer of ribonucleotides (RNA) or deoxyribonucleotides (DNA) that is single- or double-stranded, optionally containing synthetic, non-natural or altered nucleotide bases. An isolated nucleic acid fragment in the form of DNA may be comprised of one or more segments of cDNA, genomic DNA or synthetic DNA.

The terms "polynucleotide", "polynucleotide sequence", "nucleic acid sequence", and "nucleic acid fragment"/"isolated nucleic acid fragment" are used interchangeably herein. These terms encompass nucleotide sequences and the like. A polynucleotide may be a polymer of RNA or DNA that is single- or double-stranded, that optionally contains synthetic, non-natural or altered nucleotide bases. A polynucleotide in the form of a polymer of DNA may be comprised of one or more segments of cDNA, genomic DNA, synthetic DNA, or mixtures thereof. Nucleotides (usually found in their 5'-monophosphate form) are referred to by a single letter designation as follows: "A" for adenylate or deoxyadenylate (for RNA or DNA, respectively), "C" for cytidylate or deoxycytidylate, "G" for guanylate or deoxyguanylate, "U" for uridylate, "T" for deoxythymidylate, "R" for purines (A or G), "Y" for pyrimidines (C or T), "K" for G or T, "H" for A or C or T, "I" for inosine, and "N" for any nucleotide.

A "heterologous nucleic acid fragment" refers to a sequence that is not naturally occurring with the plant promoter sequence of the invention. While this nucleotide sequence is heterologous to the promoter sequence, it may be homologous, or native, or heterologous, or foreign, to the plant host. However, it is recognized that the instant promoters may be used with their native coding sequences to increase or decrease expression resulting in a change in phenotype in the transformed seed.

The terms "subfragment that is functionally equivalent" and "functionally equivalent subfragment" are used interchangeably herein. These terms refer to a portion or subsequence of an isolated nucleic acid fragment in which the ability to alter gene expression or produce a certain phenotype is retained whether or not the fragment or subfragment encodes an active enzyme. For example, the fragment or subfragment can be used in the design of chimeric genes to produce the desired phenotype in a transformed plant. Chimeric genes can be designed for use in co-suppression or antisense by linking a nucleic acid fragment or subfragment thereof, whether or not it encodes an active enzyme, in the appropriate orientation relative to a plant promoter sequence.

The terms "substantially similar" and "corresponding substantially" as used herein refer to nucleic acid fragments wherein changes in one or more nucleotide bases does not affect the ability of the nucleic acid fragment to mediate gene expression or produce a certain phenotype. These terms also refer to modifications of the nucleic acid fragments of the instant invention such as deletion or insertion of one or more nucleotides that do not substantially alter the functional properties of the resulting nucleic acid fragment relative to the initial, unmodified fragment. It is therefore understood, as those skilled in the art will appreciate, that the invention encompasses more than the specific exemplary sequences.

Moreover, the skilled artisan recognizes that substantially similar nucleic acid sequences encompassed by this invention are also defined by their ability to hybridize, under moderately stringent conditions (for example, 0.5×SSC, 0.1% SDS, 60° C.) with the sequences exemplified herein, or to any portion of the nucleotide sequences reported herein and which are functionally equivalent to the promoter of the invention. Estimates of such homology are provided by either DNA-DNA or DNA-RNA hybridization under conditions of stringency as is well understood by those skilled in the art (Hames and Higgins, Eds.; In Nucleic Acid Hybridisation; IRL Press: Oxford, U.K., 1985). Stringency conditions can be adjusted to screen for moderately similar fragments, such as homologous sequences from distantly related organisms, to highly similar fragments, such as genes that duplicate functional enzymes from closely related organisms. Post-hybridization washes partially determine stringency conditions. One set of conditions uses a series of washes starting with 6×SSC, 0.5% SDS at room temperature for 15 min, then repeated with 2×SSC, 0.5% SDS at 45° C. for 30 min, and then repeated twice with 0.2×SSC, 0.5% SDS at 50° C. for 30 min. Another set of stringent conditions uses higher temperatures in which the washes are identical to those above except for the temperature of the final two 30 min washes in 0.2×SSC, 0.5% SDS was increased to 60° C. Another set of highly stringent conditions uses two final washes in 0.1×SSC, 0.1% SDS at 65° C.

Preferred substantially similar nucleic acid sequences encompassed by this invention are those sequences that are 80% identical to the nucleic acid fragments reported herein or which are 80% identical to any portion of the nucleotide sequences reported herein. More preferred are nucleic acid fragments which are 90% identical to the nucleic acid sequences reported herein, or which are 90% identical to any portion of the nucleotide sequences reported herein. Most preferred are nucleic acid fragments which are 95% identical to the nucleic acid sequences reported herein, or which are 95% identical to any portion of the nucleotide sequences reported herein. It is well understood by one skilled in the art that many levels of sequence identity are useful in identifying related polynucleotide sequences. Useful examples of percent identities are those listed above, or also preferred is any integer percentage from 80% to 100%, such as 81%, 82%, 83%, 84%, 85%, 86%, 87%, 88%, 89%, 90%, 91%, 92%, 93%, 94%, 95%, 96%, 97%, 98 and 99%.

A "substantially homologous sequence" refers to variants of the disclosed sequences such as those that result from site-directed mutagenesis, as well as synthetically derived sequences. A substantially homologous sequence of the present invention also refers to those fragments of a particular promoter nucleotide sequence disclosed herein that operate to promote the constitutive expression of an operably linked heterologous nucleic acid fragment. These promoter fragments will comprise at least about 20 contiguous nucleotides, preferably at least about 50 contiguous nucleotides, more preferably at least about 75 contiguous nucleotides, even more preferably at least about 100 contiguous nucleotides of the particular promoter nucleotide sequence disclosed herein. The nucleotides of such fragments will usually comprise the TATA recognition sequence of the particular promoter sequence. Such fragments may be obtained by use of restriction enzymes to cleave the naturally occurring promoter nucleotide sequences disclosed herein; by synthesizing a nucleotide sequence from the naturally occurring promoter DNA sequence; or may be obtained through the use of PCR technology. See particularly, Mullis et al., Methods Enzymol. 155:335-350 (1987), and Higuchi, R. In PCR Technology: Principles and Applications for DNA Amplifications; Erlich, H. A., Ed.; Stockton Press Inc.: New York, 1989. Again, variants of these promoter fragments, such as those resulting from site-directed mutagenesis, are encompassed by the compositions of the present invention.

"Codon degeneracy" refers to divergence in the genetic code permitting variation of the nucleotide sequence without affecting the amino acid sequence of an encoded polypeptide. Accordingly, the instant invention relates to any nucleic acid fragment comprising a nucleotide sequence that encodes all or a substantial portion of the amino acid sequences set forth herein. The skilled artisan is well aware of the "codon-bias" exhibited by a specific host cell in usage of nucleotide codons to specify a given amino acid. Therefore, when synthesizing a nucleic acid fragment for improved expression in a host cell, it is desirable to design the nucleic acid fragment such that its frequency of codon usage approaches the frequency of preferred codon usage of the host cell.

Sequence alignments and percent similarity calculations may be determined using the Megalign program of the LASARGENE bioinformatics computing suite (DNASTAR Inc., Madison, Wis.) or using the AlignX program of the Vector NTI bioinformatics computing suite (Invitrogen, Carlsbad, Calif.). Multiple alignment of the sequences are performed using the Clustal method of alignment (Higgins and Sharp, CABIOS 5:151-153 (1989)) with the default parameters (GAP PENALTY=10, GAP LENGTH PENALTY=10). Default parameters for pairwise alignments and calculation of percent identity of protein sequences using the Clustal method are KTUPLE=1, GAP PENALTY=3, WINDOW=5 and DIAGONALS SAVE D=5. For nucleic acids these parameters are GAP PENALTY=10, GAP LENGTH PENALTY=10, KTUPLE=2, GAP PENALTY=5, WIN- DOW=4 and DIAGONALS SAVE D=4. A "substantial portion" of an amino acid or nucleotide sequence comprises enough of the amino acid sequence of a polypeptide or the nucleotide sequence of a gene to afford putative identification of that polypeptide or gene, either by manual evaluation of the sequence by one skilled in the art, or by computer-automated sequence comparison and identification using algorithms such as BLAST (Altschul, S. F. et al., J. Mol. Biol. 215:403-410 (1993)) and Gapped Blast (Altschul, S. F. et al., Nucleic Acids Res. 25:3389-3402 (1997)). BLASTN refers to a BLAST program that compares a nucleotide query sequence against a nucleotide sequence database.

"Gene" refers to a nucleic acid fragment that expresses a specific protein, including regulatory sequences preceding (5' non-coding sequences) and following (3' non-coding sequences) the coding sequence. "Native gene" refers to a gene as found in nature with its own regulatory sequences. "Chimeric gene" or "recombinant expression construct", which are used interchangeably, refers to any gene that is not a native gene, comprising regulatory and coding sequences that are not found together in nature. Accordingly, a chimeric gene may comprise regulatory sequences and coding sequences that are derived from different sources, or regulatory sequences and coding sequences derived from the same source, but arranged in a manner different than that found in nature. "Endogenous gene" refers to a native gene in its natural location in the genome of an organism. A "foreign" gene refers to a gene not normally found in the host organism, but that is introduced into the host organism by gene transfer. Foreign genes can comprise native genes inserted into a non-native organism, or chimeric genes. A "transgene" is a gene that has been introduced into the genome by a transformation procedure.

"Coding sequence" refers to a DNA sequence which codes for a specific amino acid sequence. "Regulatory sequences" refer to nucleotide sequences located upstream (5' non-coding sequences), within, or downstream (3' non-coding sequences) of a coding sequence, and which influence the transcription, RNA processing or stability, or translation of the associated coding sequence. Regulatory sequences may include, but are not limited to, promoters, translation leader sequences, introns, and polyadenylation recognition sequences.

"Promoter" refers to a DNA sequence capable of controlling the expression of a coding sequence or functional RNA. Functional RNA includes, but is not limited to, transfer RNA (tRNA) and ribosomal RNA (rRNA). The promoter sequence consists of proximal and more distal upstream elements, the latter elements often referred to as enhancers. Accordingly, an "enhancer" is a DNA sequence which can stimulate promoter activity and may be an innate element of the promoter or a heterologous element inserted to enhance the level or tissue-specificity of a promoter. Promoters may be derived in their entirety from a native gene, or be composed of different elements derived from different promoters found in nature, or even comprise synthetic DNA segments. It is understood by those skilled in the art that different promoters may direct the expression of a gene in different tissues or cell types, or at different stages of development, or in response to different environmental conditions. Promoters which cause a gene to be expressed in most cell types at most times are commonly referred to as "constitutive promoters". New promoters of various types useful in plant cells are constantly being discovered; numerous examples may be found in the compilation by Okamuro and Goldberg (Biochemistry of Plants 15:1-82 (1989)). It is further recognized that since in most cases the exact boundaries of regulatory sequences have not been completely defined, DNA fragments of some variation may have identical promoter activity. An "intron" is an intervening sequence in a gene that is transcribed into RNA but is then excised in the process of generating the mature mRNA. The term is also used for the excised RNA sequences. An "exon" is a portion of the sequence of a gene that is transcribed and is found in the mature messenger RNA derived from the gene, but is not necessarily a part of the sequence that encodes the final gene product.

Among the most commonly used promoters are the nopaline synthase (NOS) promoter (Ebert et al., Proc. Natl. Acad. Sci. U.S.A. 84:5745-5749 (1987)), the octapine synthase (OCS) promoter, caulimovirus promoters such as the cauliflower mosaic virus (CaMV) 19S promoter (Lawton et al., Plant Mol. Biol. 9:315-324 (1987)), the CaMV 35S promoter (Odell et al., Nature 313:810-812 (1985)), and the figwort mosaic virus 35S promoter (Sanger et al., Plant Mol. Biol. 14:433-43 (1990)), the light inducible promoter from the small subunit of rubisco, the Adh promoter (Walker et al., Proc. Natl. Acad. Sci. U.S.A. 84:6624-66280 (1987), the sucrose synthase promoter (Yang et al., Proc. Natl. Acad. Sci. U.S.A. 87:4144-4148 (1990)), the R gene complex promoter (Chandler et al., Plant Cell 1:1175-1183 (1989)), the chlorophyll a/b binding protein gene promoter, etc. Other commonly used promoters are, the promoters for the potato tuber ADPGPP genes, the sucrose synthase promoter, the granule bound starch synthase promoter, the glutelin gene promoter, the maize waxy promoter, Brittle gene promoter, and Shrunken 2 promoter, the acid chitinase gene promoter, and the zein gene promoters (15 kD, 16 kD, 19 kD, 22 kD, and 27 kD; Perdersen et al., Cell 29:1015-1026 (1982)). A plethora of promoters is described in PCT Publication No. WO 00/18963 published on Apr. 6, 2000, the disclosure of which is hereby incorporated by reference.

The "translation leader sequence" refers to a DNA sequence located between the promoter sequence of a gene and the coding sequence. The translation leader sequence is present in the fully processed mRNA upstream of the translation start sequence. The translation leader sequence may affect processing of the primary transcript to mRNA, mRNA stability or translation efficiency. Examples of translation leader sequences have been described (Turner, R. and Foster, G. D., Molecular Biotechnology 3:225 (1995)).

The "3' non-coding sequences" refer to DNA sequences located downstream of a coding sequence and include polyadenylation recognition sequences and other sequences encoding regulatory signals capable of affecting mRNA processing or gene expression. The polyadenylation signal is usually characterized by affecting the addition of polyadenylic acid tracts to the 3' end of the mRNA precursor. The use of different 3' non-coding sequences is exemplified by Ingelbrecht et al., Plant Cell 1:671-680 (1989).

"RNA transcript" refers to a product resulting from RNA polymerase-catalyzed transcription of a DNA sequence. When an RNA transcript is a perfect complementary copy of a DNA sequence, it is referred to as a primary transcript or it may be a RNA sequence derived from posttranscriptional processing of a primary transcript and is referred to as a mature RNA. "Messenger RNA" ("mRNA") refers to RNA that is without introns and that can be translated into protein by the cell. "cDNA" refers to a DNA that is complementary to and synthesized from an mRNA template using the enzyme reverse transcriptase. The cDNA can be single-stranded or converted into the double-stranded by using the Klenow fragment of DNA polymerase I. "Sense" RNA refers to RNA transcript that includes mRNA and so can be translated into protein within a cell or in vitro. "Antisense RNA" refers to a RNA transcript that is complementary to all or part of a target primary transcript or mRNA and that blocks expression or transcripts accumulation of a target gene (U.S. Pat. No. 5,107,065). The complementarity of an antisense RNA may be with any part of the specific gene transcript, i.e. at the 5' non-coding sequence, 3' non-coding sequence, introns, or the coding sequence. "Functional RNA" refers to antisense RNA, ribozyme RNA, or other RNA that may not be translated but yet has an effect on cellular processes.

The term "operably linked" refers to the association of nucleic acid sequences on a single nucleic acid fragment so that the function of one is affected by the other. For example, a promoter is operably linked with a coding sequence when it is capable of affecting the expression of that coding sequence (i.e., that the coding sequence is under the transcriptional control of the promoter). Coding sequences can be operably linked to regulatory sequences in sense or antisense orientation.

The term "expression", as used herein, refers to the production of a functional end-product e.g., a mRNA or a protein (precursor or mature).

The term "expression cassette" as used herein, refers to a discrete nucleic acid fragment into which a nucleic acid sequence or fragment can be moved.

Expression or overexpression of a gene involves transcription of the gene and translation of the mRNA into a precursor or mature protein. "Antisense inhibition" refers to the production of antisense RNA transcripts capable of suppressing the expression of the target protein. "Overexpression" refers to the production of a gene product in transgenic organisms that exceeds levels of production in normal or non-transformed organisms. "Co-suppression" refers to the production of sense RNA transcripts capable of suppressing the expression or transcript accumulation of identical or substantially similar foreign or endogenous genes (U.S. Pat. No. 5,231,020). The mechanism of co-suppression may be at the DNA level (such as DNA methylation), at the transcriptional level, or at post-transcriptional level.

Co-suppression constructs in plants previously have been designed by focusing on overexpression of a nucleic acid sequence having homology to an endogenous mRNA, in the sense orientation, which results in the reduction of all RNA having homology to the overexpressed sequence (see Vaucheret et al., Plant J. 16:651-659 (1998); and Gura, Nature 404:804-808 (2000)). The overall efficiency of this phenomenon is low, and the extent of the RNA reduction is widely variable. Recent work has described the use of "hairpin" structures that incorporate all, or part, of an mRNA encoding sequence in a complementary orientation that results in a potential "stem-loop" structure for the expressed RNA (PCT Publication No. WO 99/53050, which published on Oct. 21, 1999; and PCT Publication No. WO 02/00904, which published on Jan. 3, 2002). This increases the frequency of co-suppression in the recovered transgenic plants. Another variation describes the use of plant viral sequences to direct the suppression, or "silencing", of proximal mRNA encoding sequences (PCT Publication No. WO 98/36083, which published on Aug. 20, 1998). Genetic and molecular evidences have been obtained suggesting that dsRNA mediated mRNA cleavage may have been the conserved mechanism underlying these gene silencing phenomena (Elmayan et al., Plant Cell 10:1747-1757 (1998); Galun, In Vitro Cell. Dev. Biol. Plant 41(2):113-123 (2005); Pickford et al, Cell. Mol. Life. Sci. 60(5):871-882 (2003)).

As stated herein, "suppression" refers to a reduction of the level of enzyme activity or protein functionality (e.g., a phenotype associated with a protein) detectable in a transgenic plant when compared to the level of enzyme activity or protein functionality detectable in a non-transgenic or wild type plant with the native enzyme or protein. The level of enzyme activity in a plant with the native enzyme is referred to herein as "wild type" activity. The level of protein functionality in a plant with the native protein is referred to herein as "wild type" functionality. The term "suppression" includes lower, reduce, decline, decrease, inhibit, eliminate and prevent. This reduction may be due to a decrease in translation of the native mRNA into an active enzyme or functional protein. It may also be due to the transcription of the native DNA into decreased amounts of mRNA and/or to rapid degradation of the native mRNA. The term "native enzyme" refers to an enzyme that is produced naturally in a non-transgenic or wild type cell. The terms "non-transgenic" and "wild type" are used interchangeably herein.

"Altering expression" refers to the production of gene product(s) in transgenic organisms in amounts or proportions that differ significantly from the amount of the gene product(s) produced by the corresponding wild-type organisms (i.e., expression is increased or decreased).

"Transformation" refers to the transfer of a nucleic acid fragment into the genome of a host organism, resulting in genetically stable inheritance. Host organisms containing the transformed nucleic acid fragments are referred to as "transgenic" organisms. The preferred method of soybean cell transformation is the use of particle-accelerated or "gene gun" transformation technology (Klein, T., Nature (London) 327:70-73 (1987); U.S. Pat. No. 4,945,050).

"Transient expression" refers to the temporary expression of often reporter genes such as β-glucuronidase (GUS), fluorescent protein genes GFP, ZS-YELLOW1 N1, AM-CYAN1, DS-RED in selected certain cell types of the host organism in which the transgenic gene is introduced temporally by a transformation method. The transformed materials of the host organism are subsequently discarded after the transient gene expression assay.

Standard recombinant DNA and molecular cloning techniques used herein are well known in the art and are described more fully in Sambrook, J. et al., In Molecular Cloning: A Laboratory Manual; $2^{nd}$ ed.; Cold Spring Harbor Laboratory Press: Cold Spring Harbor, N.Y., 1989 (hereinafter "Sambrook et al., 1989") or Ausubel, F. M., Brent, R., Kingston, R. E., Moore, D. D., Seidman, J. G., Smith, J. A. and Struhl, K., Eds.; In Current Protocols in Molecular Biology; John Wiley and Sons: New York, 1990 (hereinafter "Ausubel et al., 1990").

"PCR" or "Polymerase Chain Reaction" is a technique for the synthesis of large quantities of specific DNA segments, consisting of a series of repetitive cycles (Perkin Elmer Cetus Instruments, Norwalk, Conn.). Typically, the double stranded DNA is heat denatured, the two primers complementary to the 3' boundaries of the target segment are annealed at low temperature and then extended at an intermediate temperature. One set of these three consecutive steps comprises a cycle.

A "recombinant expression construct" is a plasmid vector or a fragment thereof comprising the instant soybean constitutive promoter. The choice of plasmid vector is dependent upon the method that will be used to transform host plants. The skilled artisan is well aware of the genetic elements that must be present on the plasmid vector in order to successfully transform, select and propagate host cells containing the chimeric gene. The skilled artisan will also recognize that different independent transformation events will result in different levels and patterns of expression (Jones et al., EMBO J. 4:2411-2418 (1985); De Almeida et al., Mol. Gen. Genetics 218:78-86 (1989)), and thus that multiple events must be screened in order to obtain lines displaying the desired expression level and pattern. Such screening may be accomplished by PCR and Southern analysis of DNA, RT-PCR and Northern analysis of mRNA expression, Western analysis of protein expression, or phenotypic analysis.

The translation elongation factor EF1 alpha belongs to the GTP-binding elongation factor family and promotes the GTP-dependent binding of aminoacyl-tRNA to the A-site of ribosomes during protein biosynthesis. EF1 alpha genes and in some cases their promoters have been isolated from different plants including soybean (Aguilar et al, Plant Mol. Biol. 17(3):351-360 (1991)), *Arabidopsis* (Axelos et al, Mol. Gen. Genetics. 219:106-112 (1989)), tobacco (Aida et al, Japan Agric. Res. Quarterly 39(4):269-274 (2005)), potato (Nakane et al, J. Gen. Plant Pathol. 69:378-384 (2003)), tomato (Shewmaker et al, Nucleic Acids Res. 18(14):4276 (1990)), lily (Wang et al, J. Biol. Chem. 274(17):12001-12008 (1999)), carrot (Kawahara et al, Eur. J. Biochem. 209(1):157-162 (1992)), and other plant species. The reported EF1 alpha genes are abundant especially in fast growing plant tissues in most cases. In at least one case, the tobacco EF1 alpha gene promoter has been reported to be more efficiently to express a report transgene than the 35S promoter of cauliflower mosaic virus (Aida et al, Japan Agric. Res. Quarterly 39(4): 269-274 (2005)). It is demonstrated herein that the soybean EF1A gene promoter can, in fact, be used as a constitutive promoter to drive efficient expression of transgenes, and that such promoter can be isolated and used by one skilled in the art.

This invention concerns an isolated nucleic acid fragment comprising a constitutive elongation factor EF1 alpha gene promoter EF1A. This invention also concerns an isolated nucleic acid fragment comprising a promoter wherein said promoter consists essentially of the nucleotide sequence set forth in SEQ ID NO:1, or said promoter consists essentially of a fragment that is substantially similar and functionally equivalent to the nucleotide sequence set forth in SEQ ID NO:1. A nucleic acid fragment that is functionally equivalent to the instant EF1A promoter is any nucleic acid fragment that is capable of controlling the expression of a coding sequence or functional RNA in a similar manner to the EF1A promoter. The expression patterns of EF1A gene and its promoter are set forth in Examples 1, 2, 7, and 8.

The promoter activity of the soybean genomic DNA fragment upstream of the EF1A protein coding sequence SEQ ID NO:1 was assessed by linking the fragment to a yellow fluorescence reporter gene, ZS-YELLOW1 N1 (YFP) (Matz et al, Nat. Biotechnol. 17:969-973 (1999)), transforming the promoter:YFP expression cassette into soybean, and analyzing YFP expression in various cell types of the transgenic plants (see Example 7 and 8). YFP expression was detected in all parts of the transgenic plants though stronger expression was detected in fast growing tissues such as developing embryos and pods. These results indicated that the nucleic acid fragment contained a constitutive promoter.

It is clear from the disclosure set forth herein that one of ordinary skill in the art could perform the following procedure:

1) operably linking the nucleic acid fragment containing the EF1A promoter sequence to a suitable reporter gene; there are a variety of reporter genes that are well known to those skilled in the art, including the bacterial GUS gene, the firefly luciferase gene, and the cyan, green, red, and yellow fluorescent protein genes; any gene for which an easy and reliable assay is available can serve as the reporter gene.

2) transforming a chimeric EF1A promoter:reporter gene expression cassette into an appropriate plant for expression of the promoter. There are a variety of appropriate plants which can be used as a host for transformation that are well known to those skilled in the art, including the dicots, *Arabidopsis*, tobacco, soybean, oilseed rape, peanut, sunflower, safflower, cotton, tomato, potato, cocoa and the monocots, corn, wheat, rice, barley and palm.

3) testing for expression of the EF1A promoter in various cell types of transgenic plant tissues, e.g., leaves, roots, flowers, seeds, transformed with the chimeric EF1A promoter: reporter gene expression cassette by assaying for expression of the reporter gene product.

In another aspect, this invention concerns a recombinant DNA construct comprising at least one heterologous nucleic acid fragment operably linked to any promoter, or combination of promoter elements, of the present invention. Recombinant DNA constructs can be constructed by operably linking the nucleic acid fragment of the invention EFA1 promoter or a fragment that is substantially similar and functionally equivalent to any portion of the nucleotide sequence set forth in SEQ ID NOs:1, 2, 3, 4, 5, 6, or 7 to a heterologous nucleic acid fragment. Any heterologous nucleic acid fragment can be used to practice the invention. The selection will depend upon the desired application or phenotype to be achieved. The various nucleic acid sequences can be manipulated so as to provide for the nucleic acid sequences in the proper orientation. It is believed that various combinations of promoter elements as described herein may be useful in practicing the present invention.

In another aspect, this invention concerns a recombinant DNA construct comprising at least one acetolactate synthase (ALS) nucleic acid fragment operably linked to EF1A promoter, or combination of promoter elements, of the present invention. The acetolactate synthase gene is involved in the biosynthesis of branched chain amino acids in plants and is the site of action of several herbicides including sulfonyl urea. Expression of a mutated acetolactate synthase gene encoding a protein that can no longer bind the herbicide will enable the transgenic plants to be resistant to the herbicide (U.S. Pat. No. 5,605,011, U.S. Pat. No. 5,378,824). The mutated acetolactate synthase gene is also widely used in plant transformation to select transgenic plants.

In another embodiment, this invention concerns host cells comprising either the recombinant DNA constructs of the invention as described herein or isolated polynucleotides of the invention as described herein. Examples of host cells which can be used to practice the invention include, but are not limited to, yeast, bacteria, and plants.

Plasmid vectors comprising the instant recombinant expression construct can be constructed. The choice of plasmid vector is dependent upon the method that will be used to transform host cells. The skilled artisan is well aware of the genetic elements that must be present on the plasmid vector in order to successfully transform, select and propagate host cells containing the chimeric gene.

Methods for transforming dicots, primarily by use of *Agrobacterium tumefaciens*, and obtaining transgenic plants have been published, among others, for cotton (U.S. Pat. No. 5,004,863, U.S. Pat. No. 5,159,135); soybean (U.S. Pat. No. 5,569,834, U.S. Pat. No. 5,416,011); *Brassica* (U.S. Pat. No. 5,463,174); peanut (Cheng et al., Plant Cell Rep. 15:653-657 (1996), McKently et al., Plant Cell Rep. 14:699-703 (1995)); papaya (Ling et al., Bio/technology 9:752-758 (1991)); and pea (Grant et al., Plant Cell Rep. 15:254-258 (1995)). For a review of other commonly used methods of plant transformation see Newell, C. A., Mol. Biotechnol. 16:53-65 (2000). One of these methods of transformation uses *Agrobacterium rhizogenes* (Tepfler, M. and Casse-Delbart, F., Microbiol. Sci.

4:24-28 (1987)). Transformation of soybeans using direct delivery of DNA has been published using PEG fusion (PCT Publication No. WO 92/17598), electroporation (Chowrira et al., Mol. Biotechnol. 3:17-23 (1995); Christou et al., Proc. Natl. Acad. Sci. U.S.A. 84:3962-3966 (1987)), microinjection, or particle bombardment (McCabe et al., Bio/Technology 6:923 (1988); Christou et al., Plant Physiol. 87:671-674 (1988)).

There are a variety of methods for the regeneration of plants from plant tissues. The particular method of regeneration will depend on the starting plant tissue and the particular plant species to be regenerated. The regeneration, development and cultivation of plants from single plant protoplast transformants or from various transformed explants is well known in the art (Weissbach and Weissbach, Eds.; In Methods for Plant Molecular Biology; Academic Press, Inc.: San Diego, Calif., 1988). This regeneration and growth process typically includes the steps of selection of transformed cells, culturing those individualized cells through the usual stages of embryonic development or through the rooted plantlet stage. Transgenic embryos and seeds are similarly regenerated. The resulting transgenic rooted shoots are thereafter planted in an appropriate plant growth medium such as soil. Preferably, the regenerated plants are self-pollinated to provide homozygous transgenic plants. Otherwise, pollen obtained from the regenerated plants is crossed to seed-grown plants of agronomically important lines. Conversely, pollen from plants of these important lines is used to pollinate regenerated plants. A transgenic plant of the present invention containing a desired polypeptide is cultivated using methods well known to one skilled in the art.

In addition to the above discussed procedures, practitioners are familiar with the standard resource materials which describe specific conditions and procedures for the construction, manipulation and isolation of macromolecules (e.g., DNA molecules, plasmids, etc.), generation of recombinant DNA fragments and recombinant expression constructs and the screening and isolating of clones, (see for example, Sambrook, J. et al., In Molecular Cloning: A Laboratory Manual; $2^{nd}$ ed.; Cold Spring Harbor Laboratory Press: Cold Spring Harbor, N.Y., 1989; Maliga et al., In Methods in Plant Molecular Biology; Cold Spring Harbor Press, 1995; Birren et al., In Genome Analysis: Detecting Genes, 1; Cold Spring Harbor: New York, 1998; Birren et al., In Genome Analysis: Analyzing DNA, 2; Cold Spring Harbor: New York, 1998; Clark, Ed., In Plant Molecular Biology: A Laboratory Manual; Springer: New York, 1997).

The skilled artisan will also recognize that different independent transformation events will result in different levels and patterns of expression of the chimeric genes (Jones et al., EMBO J. 4:2411-2418 (1985); De Almeida et al., Mol. Gen. Genetics 218:78-86 (1989)). Thus, multiple events must be screened in order to obtain lines displaying the desired expression level and pattern. Such screening may be accomplished by Northern analysis of mRNA expression, Western analysis of protein expression, or phenotypic analysis. Also of interest are seeds obtained from transformed plants displaying the desired gene expression profile.

The level of activity of the EF1A promoter is comparable to that of many known strong promoters, such as the CaMV 35S promoter (Atanassova et al., Plant Mol. Biol. 37:275-285 (1998); Battraw and Hall, Plant Mol. Biol. 15:527-538 (1990); Holtorf et al., Plant Mol. Biol. 29:637-646 (1995); Jefferson et al., EMBO J. 6:3901-3907 (1987); Wilmink et al., Plant Mol. Biol. 28:949-955 (1995)), the *Arabidopsis* oleosin promoters (Plant et al., Plant Mol. Biol. 25:193-205 (1994); Li, Texas A&M University Ph.D. dissertation, pp. 107-128 (1997)), the *Arabidopsis* ubiquitin extension protein promoters (Callis et al., J. Biol. Chem. 265(21):12486-12493 (1990)), a tomato ubiquitin gene promoter (Rollfinke et al., Gene 211:267-276 (1998)), a soybean heat shock protein promoter, and a maize H3 histone gene promoter (Atanassova et al., Plant Mol. Biol. 37:275-285 (1998)). Universal expression of chimeric genes in most plant cells makes the EF1A promoter of the instant invention especially useful when constitutive expression of a target heterologous nucleic acid fragment is required.

Another general application of the EF1A promoter of the invention is to construct chimeric genes that can be used to reduce expression of at least one heterologous nucleic acid fragment in a plant cell. To accomplish this, a chimeric gene designed for gene silencing of a heterologous nucleic acid fragment can be constructed by linking the fragment to the EF1A promoter of the present invention. (See U.S. Pat. No. 5,231,020, and PCT Publication No. WO 99/53050, which published on Oct. 21, 1999, PCT Publication No. WO 02/00904, which published on Jan. 3, 2002, and PCT Publication No. WO 98/36083, which published on Aug. 20, 1998, for methodology to block plant gene expression via cosuppression.) Alternatively, a chimeric gene designed to express antisense RNA for a heterologous nucleic acid fragment can be constructed by linking the fragment in reverse orientation to the EF1A promoter of the present invention. (See U.S. Pat. No. 5,107,065 for methodology to block plant gene expression via antisense RNA.) Either the cosuppression or antisense chimeric gene can be introduced into plants via transformation. Transformants wherein expression of the heterologous nucleic acid fragment is decreased or eliminated are then selected.

This invention also concerns a method of altering (increasing or decreasing) the expression of at least one heterologous nucleic acid fragment in a plant cell which comprises:

(a) transforming a plant cell with the recombinant expression construct described herein;

(b) growing fertile mature plants from the transformed plant cell of step (a);

(c) selecting plants containing a transformed plant cell wherein the expression of the heterologous nucleic acid fragment is increased or decreased.

Transformation and selection can be accomplished using methods well-known to those skilled in the art including, but not limited to, the methods described herein.

EXAMPLES

The present invention is further defined in the following Examples, in which parts and percentages are by weight and degrees are Celsius, unless otherwise stated. Sequences of promoters, cDNA, adaptors, and primers listed in this invention all are in the 5' to 3' orientation unless described otherwise. Techniques in molecular biology were typically performed as described in Ausubel, F. M. et al., In Current Protocols in Molecular Biology; John Wiley and Sons: New York, 1990 or Sambrook, J. et al., In Molecular Cloning: A Laboratory Manual; $2^{nd}$ ed.; Cold Spring Harbor Laboratory Press: Cold Spring Harbor, N.Y., 1989 (hereinafter "Sambrook et al., 1989"). It should be understood that these Examples, while indicating preferred embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various usages and conditions. Thus, various modifications of the invention in addition to those shown and described herein will be apparent to those skilled in the art from the foregoing description. Such modifications are also intended to fall within the scope of the appended claims.

The disclosure of each reference set forth herein is incorporated herein by reference in its entirety.

Example 1

Identification of Soybean Constitutive Promoter Candidate Genes

Soybean expression sequence tags (EST) were generated by sequencing randomly selected clones from cDNA libraries constructed from different soybean tissues. Multiple EST sequences could often be found with different lengths representing the different regions of the same soybean gene. If more EST sequences representing the same gene are more frequently found from a tissue-specific cDNA library such as a flower library than from a leaf library, there is a possibility that the represented gene could be a flower preferred gene candidate. Likewise, if similar numbers of ESTs for the same gene were found in various libraries constructed from different tissues, the represented gene could be a constitutively expressed gene. Multiple EST sequences representing the same soybean gene could be compiled electronically based on their overlapping sequence homology into a unique full length sequence representing the gene. These assembled unique gene sequences were accumulatively collected in Pioneer Hi-Bred Int'l proprietary searchable databases. To identify strong constitutive promoter candidate genes, searches were performed to look for gene sequences that were found at similar frequencies in leaf, root, flower, embryos, pod, and also in other libraries. One unique gene PSO467151 was identified in the search to be a constitutive gene candidate. PSO467151 cDNA sequence (SEQ ID NO:21) as well as its putative translated protein sequence (SEQ ID NO:22) were used to search National Center for Biotechnology Information (NCBI) databases. Both PSO467151 nucleotide and amino acid sequences were found to have high homology to translation elongation factor EF1 alpha genes discovered in several plants including soybean (Aguilar et al, Plant Mol. Biol. 17(3):351-360 (1991)).

Due to the limited number of ESTs representing PSO467151 in the databases, it was necessary to apply an additional analysis to confirm its gene expression profile. A more sensitive gene expression profiling methodology MPSS (Mass Parallel Signature Sequence) transcript profiling technique (Brenner et al., Proc Natl Acad Sci USA 97:1665-70 (2000)) was used to confirm that PSO467151 is indeed constitutively expressed. The MPSS technology involves the generation of 17 base signature tags from mRNA samples that have been reverse transcribed from poly A+ RNA isolated using standard molecular biology techniques (Sambrook et al., 1989). The tags are simultaneously sequenced and assigned to genes or ESTs. The abundance of these tags is given a number value that is normalized to parts per million (PPM) which then allows the tag expression, or tag abundance, to be compared across different tissues. Thus, the MPSS platform can be used to determine the expression pattern of a particular gene and its expression levels in different tissues. MPSS gene expression profiles generated from different soybean tissues over the time have been accumulatively collected in Pioneer Hi-Bred Int'l proprietary searchable databases. The PSO467151 cDNA sequence was first used to search the databases to identify a MPSS tag that was unique and identical to a 17 base pair region in the 3' end of the PSO467151 cDNA sequence (SEQ ID NO: 43). The sequence tag was then used to search the databases again to reveal its abundance in different tissues. As illustrated in Table 1, the PSO467151 gene was confirmed to be highly abundant in all tissues, a desired expression profile for its promoter to be used as a constitutive promoter with stronger expression in seed and pod.

TABLE 1

Lynx MPSS Expression Profiles of the PSO467151 Gene

| | |
|---|---|
| Target gene | PSO467151 |
| Tag sequence | SEQ ID NO: 43 |
| Flower | 1869 |
| Pod | 7176 |
| Flower bud | 2191 |
| Lateral root | 3112 |
| Leaf | 3068 |
| Petiole | 1716 |
| Primary root | 2910 |
| Seed | 7584 |
| Stem | 2198 |

Example 2

Quantitative RT-PCR Profiles of EF1a Gene Expression in Soybean

The MPSS profile of PSO467151 was confirmed and extended by analyzing 14 different soybean tissues using the relative quantitative RT-PCR technique with a ABI7500 real time PCR system (Applied Biosystems, Foster City, Calif.). Fourteen soybean tissues, somatic embryo, somatic embryo one week on charcoal plate, leaf, leaf petiole, root, flower bud, open flower, R3 pod, R4 seed, R4 pod coat, R5 seed, R5 pod coat, R6 seed, R6 pod coat were collected from cultivar 'Jack' and flash frozen in liquid nitrogen. The seed and pod development stages were defined according to descriptions in Fehr and Caviness, IWSRBC 80:1-12 (1977). Total RNA was extracted with Trizol reagents (Invitrogen, Carlsbad, Calif.) and treated with DNase I to remove any trace amount of genomic DNA contamination. The first strand cDNA was synthesized using the Superscript III reverse transcriptase (Invitrogen). Regular PCR analysis was done to confirm that the cDNA was free of any genomic DNA using primers shown in SEQ ID NO:26 and 27.

Figure 1:
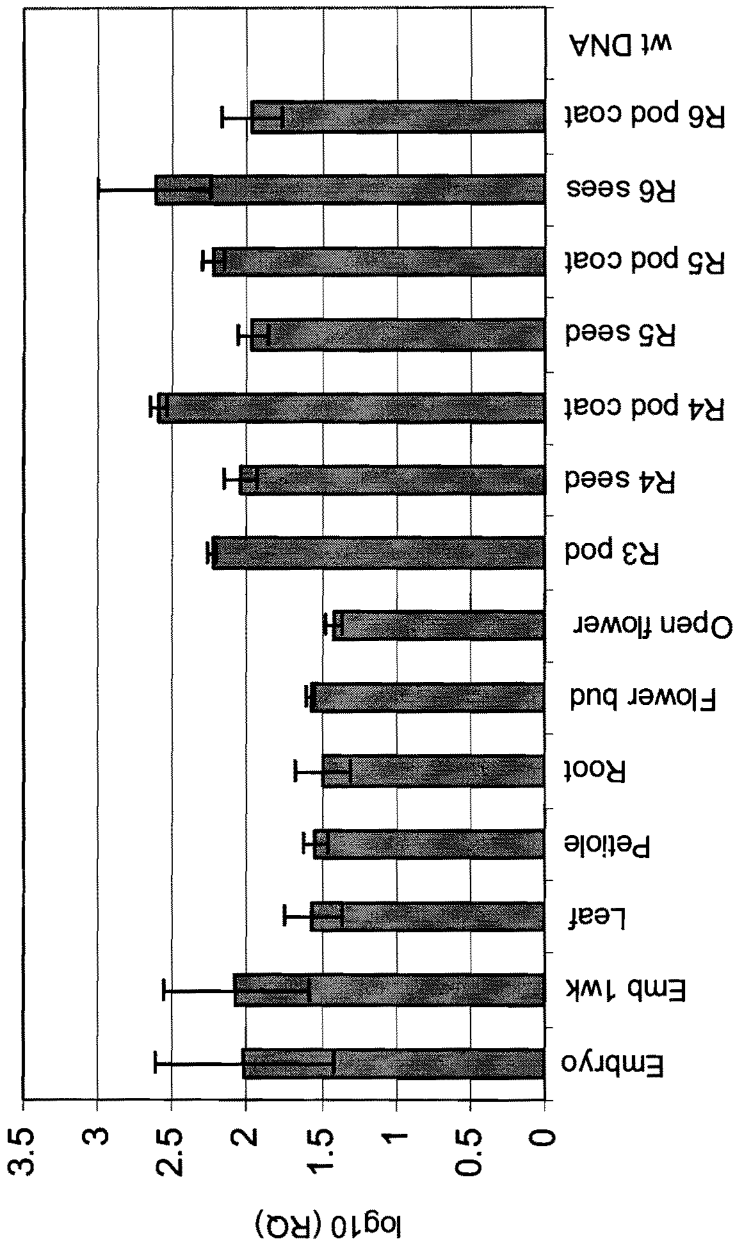
FIG. 1 is the logarithm of relative quantifications of the soybean EF1A gene expression in 14 different soybean tissues by quantitative RT-PCR. The gene expression profile indicates that the EF1A gene is highly expressed in all the checked tissues.

The primers are specific to the 5'UTR intron/exon junction region of a soybean S-adenosylmethionine synthetase gene promoter SAMS (Falco and Li, WO 00/37662 (2000)). PCR using this primer set will amplify a 967 bp DNA fragment from any soybean genomic DNA template and a 376 bp DNA fragment from the cDNA template. Genome DNA free cDNA aliquots were used in quantitative RT-PCR analysis in which an endogenous soybean ATP sulfurylase gene was used as an internal control and wild type soybean genomic DNA was used as the calibrator for relative quantification. PCR reaction data were captured and analyzed using the sequence detection software provided with the ABI7500 real time PCR system. The qRT-PCR profiling of the PSO467151 EF1A gene expression confirmed its strong and constitutive expression pattern (FIG. 1).

Example 3

Isolation of Soybean EF1A Promoter

PSO467151 sequence was used to search the Pioneer Hi-Bred Int'l propriety EST databases and a BAC (bacterial artificial chromosome) clone sbacm.pk087.m18 was identified based on sequence similarity. The BAC clone was partially sequenced to reveal a approximately 2.5 Kb sequence upstream of PSO467151 EF1A gene coding region. The primers shown in SEQ ID NO:19 and 20 were then designed to amplify the putative full length 2181 bp EF1A promoter from the BAC clone DNA using a polymerase chain reaction (PCR). SEQ ID NO:19 contains a recognition site for the restriction enzyme XmaI. SEQ ID NO:20 contains a recognition site for the restriction enzyme NcoI. In order to study promoter function, the EF1A promoter was cloned into an expression vector via the restriction enzymes sites.

PCR cycle conditions were 94° C. for 4 minutes; 35 cycles of 94° C. for 30 seconds, 60° C. for 1 minute, and 68° C. for 2 minutes; and a final 68° C. for 5 minutes before holding at 4° C. The PCR reaction was resolved using agarose gel electrophoresis to identify the right size PCR product representing the ~2.1 Kb EF1A promoter. The PCR amplified DNA of the correct size was then digested with XmaI and NcoI restriction enzymes and the fragment was cloned into a Gateway (Invitrogen) cloning entry vector by conventional ligation to place the putative EF1A promoter upstream of the ZS-YELLOW N1 fluorescent reporter gene (YFP). Several clones containing the ~2.1 Kb DNA insert were sequenced and construct QC314 (FIG. 3) was confirmed to contain the identical EF1A promoter sequence as previously sequenced from the BAC clone sbacm.pk087.m18. The EF1A promoter sequence is herein listed as SEQ ID NO:1.

Sequence alignment analysis between the EF1A promoter sequence and the full length EF1 alpha cDNA sequence revealed that there is a 770 bp intron SEQ ID NO:16 in the 5'UTR (un-translated region). The promoter region upstream of the putative 5'UTR is 1344 bp long. The 5'UTR is interrupted by the intron into a 54 bp fragment SEQ ID NO:17 upstream of the intron and a 13 bp fragment SEQ ID NO:18 downstream of the intron. The last two base pairs CC in the 13 bp fragment are extra base pairs introduced as part of the cloning site NcoI CCATGG. The two 5'UTR fragments, the 5'UTR intron, and the upstream promoter region with a total of 2181 bp nucleotides (SEQ ID NO:1) are herein collectively called EF1A promoter.

Example 4

EF1A Promoter Copy Number Analysis

Southern hybridization analysis was performed to examine whether additional copies or sequences with significant similarity to the EF1A promoter exist in the soybean genome. Soybean 'Jack' wild type genomic DNA was digested with nine different restriction enzymes, BamHI, BglII, DraI, EcoRI, EcoRV, HindIII, MfeI, NdeI, and SpeI and distributed in a 0.7% agraose gel by electrophoresis. The DNA was blotted onto Nylon membrane and hybridized at 50° C. with digoxigenin labeled EF1A promoter DNA probe in EasyHyb Southern hybridization solution, and subsequentially washed 10 minutes with 2×SSC/0.1% SDS at room temperature and 3×10 minutes at 65° C. with 0.1×SSC/0.1% SDS according to the protocol provided by the manufacturer (Roche Applied Science, Indianapolis, Ind.). The EF1A promoter probe was labeled by PCR using the DIG DNA labeling kit (Roche Applied Science) with two gene specific primers SEQ ID NO:15 and SEQ ID NO:8 to make a 837 bp long probe SEQ ID NO:7 covering the EF1A 5'UTR and its 5'UTR intron.

Figure 2:
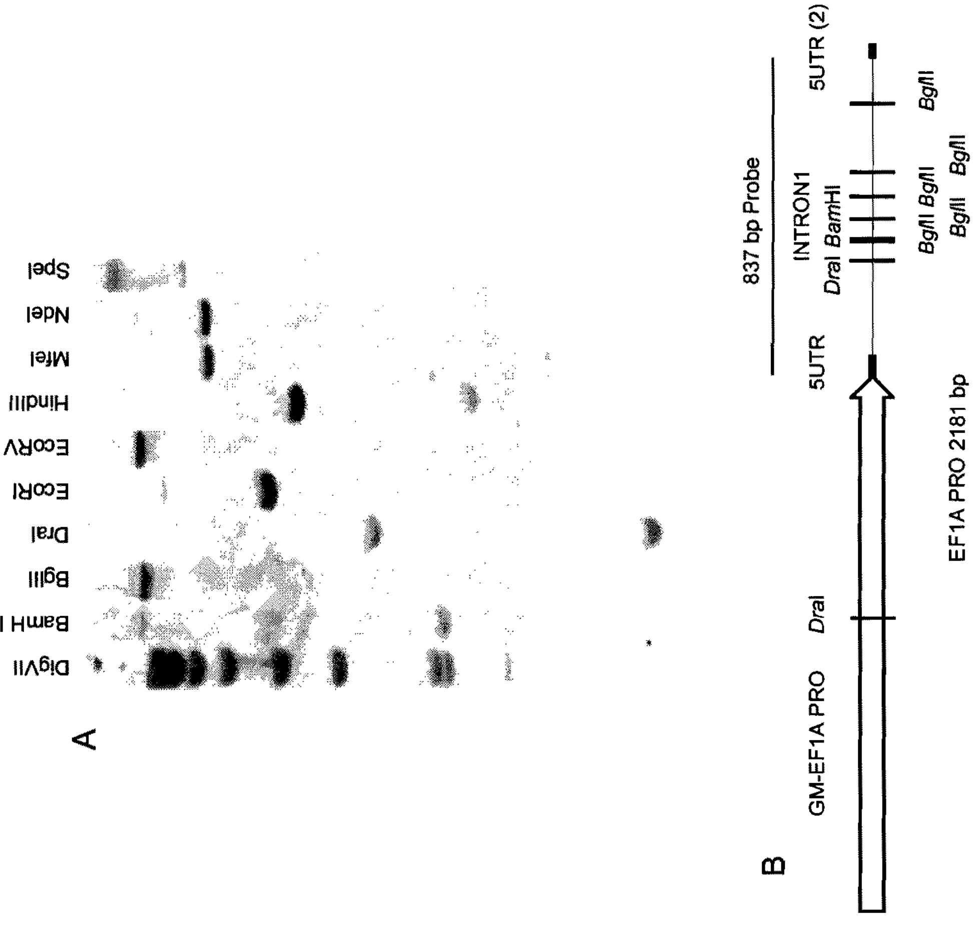
FIG. 2 is EF1A promoter copy number analysis by Southern.

According to the EF1A promoter sequence, restriction enzymes EcoRI, EcoRV, HindIII, MfeI, NdeI, and SpeI do not cut the probe region, therefore only one band would be expected to hybridize to the probe for each of the six digestions if only one copy of EF1A sequence exists in the soybean genome (FIG. 2B). The observation that, in addition to a strong major band, a weak minor band hybridized for EcoRI, MfeI, NdeI, and SpeI digestions and two weak bands hybridized for HindIII digestion suggested that there is another sequence in the soybean genome with enough similarity to the 837 bp EF1A probe sequence to hybridize to the probe (FIG. 2A).

Each of the three enzymes, BamHI, BglII, and DraI cuts the EF1A probe region at least once, therefore the presence of two or more bands would be expected after digestion with each one of these enzymes. BamHI cuts only the probe region once roughly in the middle; two bands with unspecified sizes were expected and observed. In addition, a weak band was also observed suggesting the existence of another similar sequence in addition to the EF1A probe in soybean genome. BglII cuts five times in the probe region but only bands larger than ~900 bp would have been retained and transferred onto the Southern blot after gel electrophoresis. A strong major band and two weak bands were observed for BglII digestion, also suggesting the existence of another soybean genomic DNA sequence similar to the EF1A probe. DraI cuts the probe region once roughly in the middle and also several times in the upstream region, a 937 bp band and another band with unspecified size were expected and observed. In conclusion, Southern blot analysis suggested the existence of another sequence with enough similarity to the EF1A promoter to hybridize to the same EF1A probe under the described Southern hybridization conditions

Example 5

EF1A:YFP Reporter Gene Constructs and Soybean Transformation

Figure 3:
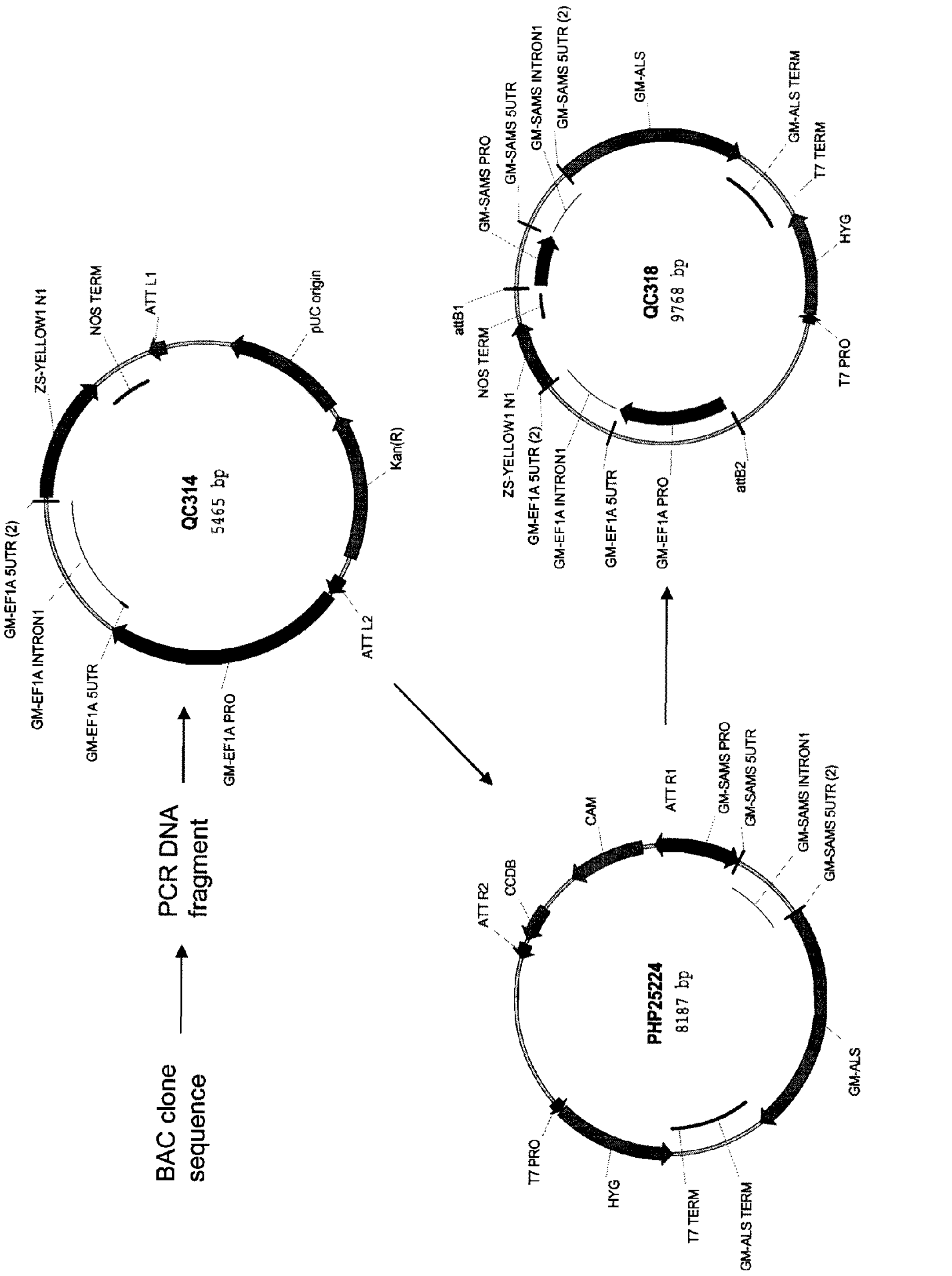
FIG. 3 are the maps of plasmid QC314, PHP25224, and QC318.

The EF1A:YFP expression cassette in Gateway entry construct QC314 (SEQ ID NO:23) described in EXAMPLE 3 was moved into a Gateway destination vector PHP25224 by LR clonase mediated DNA recombination between the attL1 and attL2 recombination sites (SEQ ID NO:37, and 38, respectively) in QC314 and the attR1-attR2 recombination sites (SEQ ID NO:39, and 40, respectively) in PHP25224 (Invitrogen). Since the destination vector PHP25224 already contains a soybean transformation selectable marker gene SAMS:ALS, the resulting DNA construct QC318 (SEQ ID NO:24) has two gene expression cassettes EF1A:YFP and SAMS:ALS linked together (FIG. 3). Two 21 bp recombination sites attB1 and attB2 (SEQ ID NO:41, and 42, respectively) were newly created recombination sites resulting from DNA recombination between attL1 and attR2, and between attL2 and attR2, respectively. The 7524 bp DNA fragment containing the linked EF1A:YFP and SAMS:ALS expression cassettes was isolated from plasmid QC318 with AscI digestion, separated from the vector backbone fragment by agarose gel electrophoresis, and purified from the gel with a DNA gel extraction kit (Qiagen, Valencia, Calif.). The purified DNA fragment was transformed to soybean cultivar Jack by the method of particle gun bombardment (Klein et al., Nature 327:70-73 (1987); U.S. Pat. No. 4,945,050) to study the EF1 A1 promoter activity in stably transformed soybean plants.

The same methodology as outlined above for the EF1A:YFP expression cassette construction and transformation can be used with other heterologous nucleic acid sequences encoding for example a reporter protein, a selection marker, a protein conferring disease resistance, protein conferring herbicide resistance, protein conferring insect resistance; protein involved in carbohydrate metabolism, protein involved in fatty acid metabolism, protein involved in amino acid metabolism, protein involved in plant development, protein involved in plant growth regulation, protein involved in yield improvement, protein involved in drought resistance, protein involved in cold resistance, protein involved in heat resistance and salt resistance in plants.

Soybean somatic embryos from the Jack cultivar were induced as follows. Cotyledons (~3 mm in length) were dissected from surface sterilized, immature seeds and were cultured for 6-10 weeks in the light at 26° C. on a Murashige and Skoog media containing 0.7% agar and supplemented with 10 mg/ml 2,4-D. Globular stage somatic embryos, which produced secondary embryos, were then excised and placed into flasks containing liquid MS medium supplemented with 2,4-D (10 mg/ml) and cultured in the light on a rotary shaker. After repeated selection for clusters of somatic embryos that multiplied as early, globular staged embryos, the soybean embryogenic suspension cultures were maintained in 35 ml liquid media on a rotary shaker, 150 rpm, at 26° C. with fluorescent lights on a 16:8 hour day/night schedule. Cultures were subcultured every two weeks by inoculating approximately 35 mg of tissue into 35 ml of the same fresh liquid MS medium.

Soybean embryogenic suspension cultures were then transformed by the method of particle gun bombardment using a DuPont Biolistic™ PDS1000/HE instrument (Bio-Rad Laboratories, Hercules, Calif.). To 50 μl of a 60 mg/ml 1.0 mm gold particle suspension were added (in order): 30 μl of 10 ng/μl QC318 DNA fragment EF1A:YFP+SAMS:ALS, 20 μl of 0.1 M spermidine, and 25 μl of 5 M $CaCl_2$. The particle preparation was then agitated for 3 minutes, spun in a centrifuge for 10 seconds and the supernatant removed. The DNA-coated particles were then washed once in 400 μl 100% ethanol and resuspended in 45 μl of 100% ethanol. The DNA/particle suspension was sonicated three times for one second each. 5 μl of the DNA-coated gold particles was then loaded on each macro carrier disk.

Approximately 300-400 mg of a two-week-old suspension culture was placed in an empty 60×15 mm Petri dish and the residual liquid removed from the tissue with a pipette. For each transformation experiment, approximately 5 to 10 plates of tissue were bombarded. Membrane rupture pressure was set at 1100 psi and the chamber was evacuated to a vacuum of 28 inches mercury. The tissue was placed approximately 3.5 inches away from the retaining screen and bombarded once. Following bombardment, the tissue was divided in half and placed back into liquid media and cultured as described above.

Five to seven days post bombardment, the liquid media was exchanged with fresh media containing 100 ng/ml chlorsulfuron as selection agent. This selective media was refreshed weekly. Seven to eight weeks post bombardment, green, transformed tissue was observed growing from untransformed, necrotic embryogenic clusters. Isolated green tissue was removed and inoculated into individual flasks to generate new, clonally propagated, transformed embryogenic suspension cultures. Each clonally propagated culture was treated as an independent transformation event and subcultured in the same liquid MS media supplemented with 2,4-D (10 mg/ml) and 100 ng/ml chlorsulfuron selection agent to increase mass. The embryogenic suspension cultures were then transferred to agar solid MS media plates without 2,4-D supplement to allow somatic embryos to develop. A sample of each event was collected at this stage for PCR and quantitative PCR analysis.

Cotyledon stage somatic embryos were dried-down (by transferring them into an empty small Petri dish that was seated on top of a 10 cm Petri dish containing some agar gel to allow slow dry down) to mimic the last stages of soybean seed development. Dried-down embryos were placed on germination solid media and transgenic soybean plantlets were regenerated. The transgenic plants were then transferred to soil and maintained in growth chambers for seed production. Genomic DNA were extracted from somatic embryo samples and analyzed by quantitative PCR using the 7500 real time PCR system (Applied Biosystems) with gene-specific primers and FAM-labeled fluorescence probes to check copy numbers of both the SAMS:ALS expression cassette and the EF1A:YFP expression cassette. The qPCR analysis was done in duplex reactions with a heat shock protein (HSP) gene as the endogenous controls and a transgenic DNA sample with a known single copy of SAMS:ALS or YFP transgene as the calibrator using the relative quantification methodology (Applied Biosystems). The endogenous control HSP probe was labeled with VIC and the target gene SAMS or YFP probe was labeled with FAM for the simultaneous detection of both fluorescent probes in the same duplex reactions. FAM labeled DNA oligo probes and VIC labeled oligo probes were obtained from Sigma Genosy (The Woodlands, Tex.).

The primers and probes used in the qPCR analysis are listed below.

SAMS forward primer: SEQ ID NO:28
FAM labeled SAMS probe: SEQ ID NO:29
SAMS reverse primer: SEQ ID NO:30
YFP forward primer: SEQ ID NO:31
FAM labeled YFP probe: SEQ ID NO:32
YFP reverse primer: SEQ ID NO:33
HSP forward primer: SEQ ID NO:34
VIC labeled HSP probe: SEQ ID NO:35
HSP reverse primer: SEQ ID NO:36

Only transgenic soybean events containing 1 or 2 copies of both the SAMS:ALS expression cassette and the EF1A:YFP expression cassette were selected for further gene expression evaluation and seed production (see Table 2). Events negative for YFP qPCR or with more than 2 copies for the SAMS qPCR were not further followed. YFP expressions are described in detail in EXAMPLE 8 and are recorded in Table 2.

TABLE 2

Relative transgene copy numbers and YFP expression of EF1A:YFP transgenic plants

| Event ID | YFP | YFP qPCR | SAMS qPCR |
|---|---|---|---|
| 4870.2.1 | + | 1.2 | 0.6 |
| 4870.2.2 | + | 1.0 | 0.7 |
| 4870.2.4 | + | 1.0 | 0.6 |
| 4870.2.6 | + | 1.3 | 0.6 |
| 4870.2.7 | + | 1.0 | 0.7 |
| 4870.2.8 | + | 1.0 | 0.5 |
| 4870.3.1 | + | 1.0 | 0.6 |
| 4870.3.2 | + | 1.0 | 0.4 |
| 4870.3.4 | + | 1.4 | 0.7 |
| 4870.3.5 | + | 1.3 | 0.5 |
| 4870.4.1 | + | 1.8 | 1.0 |
| 4870.6.1 | + | 0.9 | 0.5 |
| 4870.6.3 | + | 1.1 | 0.8 |
| 4870.6.4 | + | 1.0 | 0.5 |
| 4870.6.5 | + | 1.0 | 0.5 |
| 4870.6.9 | + | 1.1 | 0.7 |
| 4870.7.1 | + | 1.1 | 0.5 |
| 4870.8.1 | + | 1.8 | 1.3 |
| 4870.8.3 | + | 1.0 | 0.7 |
| 4870.8.5 | + | 1.7 | 1.3 |
| 4870.8.7 | + | 1.7 | 1.2 |

Example 6

Construction of EF1A Promoter Deletion Constructs

Figure 4:
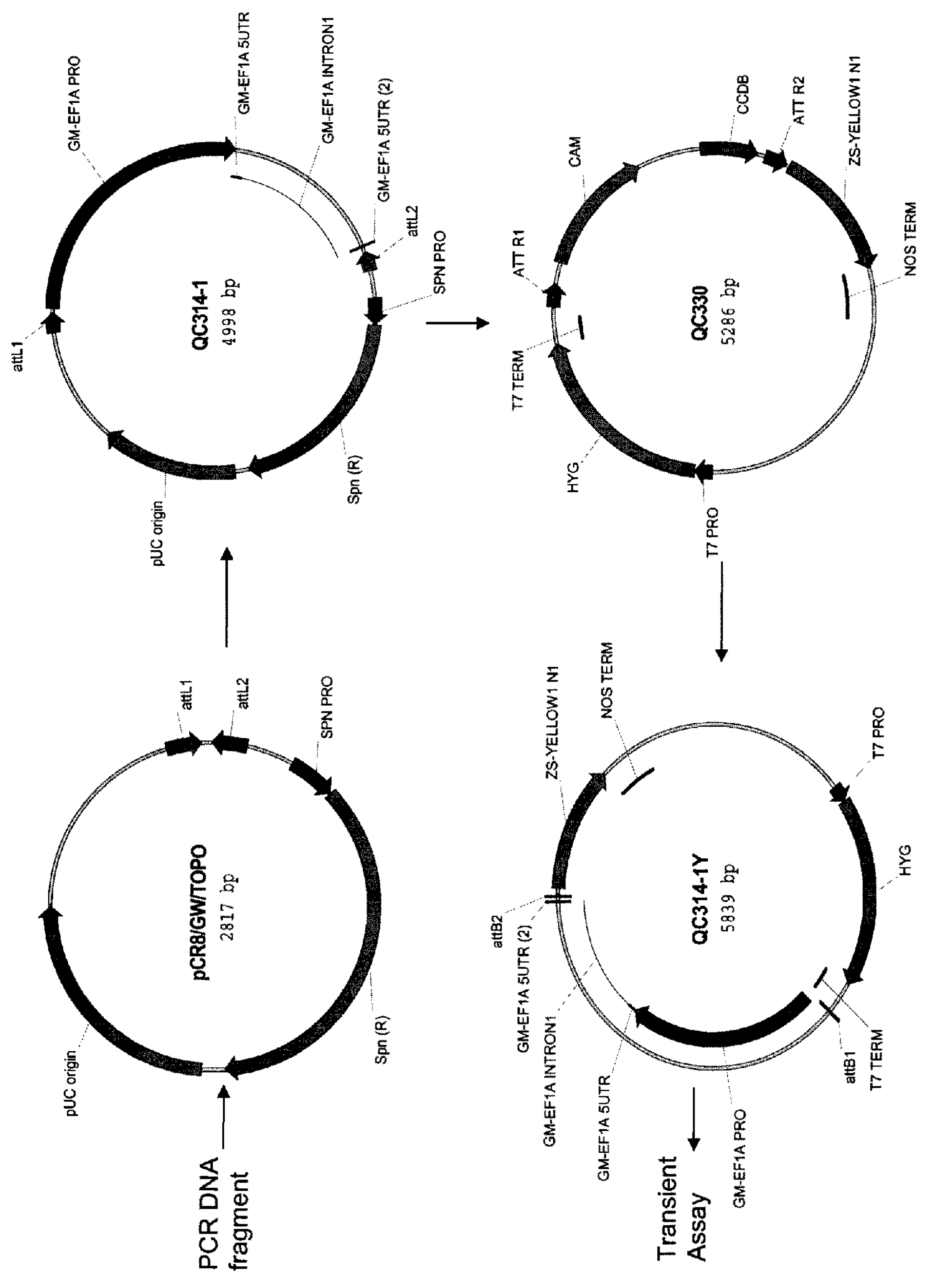
FIG. 4 are the maps of plasmid pCR8/GW/TOPO, QC314-1, QC300, and QC314-1Y containing the full length 2181 bp EF1A promoter. Promoter deletion constructs QC314-2Y, QC314-3Y, QC314-4Y, QC314-5Y, QC314-6Y, and QC314-7Y containing the 1841, 1642, 1431, 1215, 1012, and 837 bp truncated EF1A promoters, respectively, have the similar map configuration.

To define the transcriptional elements controlling the EF1A promoter activity, the 2181 bp full length (SEQ ID NO:1) and six 5' unidirectional deletion fragments 1841 bp, 1642 bp, 1431 bp, 1215 bp, 1012, and 837 bp in length corresponding to SEQ ID NO:2, 3, 4, 5, 6, and 7, respectively, were made by PCR amplification from the full length soybean EF1A promoter contained in the original construct QC314 (FIG. 3). The same antisense primer (SEQ ID NO:8) was used in the amplification by PCR of all the seven EF1A promoter fragments (SEQ ID NO:1, 2, 3, 4, 5, 6, and 7) by pairing with different sense primers SEQ ID NOs:9, 10, 11, 12, 13, 14, and 15, respectively. Each of the PCR amplified promoter DNA fragments was cloned into the Gateway cloning ready TA cloning vector pCR8/GW/TOPO (Invitrogen) and clones with the correct orientation, relative to the Gateway recombination sites attL1 and attL2, were selected by BamHI+XhoI double restriction enzymes digestion analysis and sequence confirmation (see the example map QC314-1 in FIG. 4). The maps of constructs QC314-2, 3, 4, 5, 6, and 7 containing the EF1A promoter fragments SEQ ID NOs:2, 3, 4, 5, 6, 7 are similar to QC314-1 map and are not shown. The promoter fragment in the right orientation was subsequently cloned into a Gateway destination vector QC300 by Gateway LR clonase reaction (Invitrogen) to place the promoter fragment in front of the reporter gene YFP (see the example map QC314-1Y in FIG. 4). A 21 bp Gateway recombination site attB2 SEQ ID NO:42 was inserted between the promoter and the YFP reporter gene coding region as a result of the Gateway cloning process. The maps of constructs QC314-2Y, 3Y, 4Y, 5Y, 6Y, and 7Y containing the EF1A promoter fragments SEQ ID NOs:2, 3, 4, 5, 6, and 7 are similar to QC314-1Y map and not shown. The EF1A:YFP promoter deletion constructs were delivered into germinating soybean cotyledons by gene gun bombardment for transient gene expression study. The full length EF1A promoter in QC314 without the attB2 site located between the promoter and the YFP gene was included as a positive control for transient expression analysis. The seven EF1A promoter fragments analyzed are schematically described in FIG. 5.

Example 7

Transient Expression Analysis of EF1A:YFP Constructs

The constructs containing the full length and partial promoter fragments (QC314, QC314-1Y, 2Y, 3Y, 4Y, 5Y, 6Y, and 7Y) were tested by transiently expressing the ZS-YELLOW1 N1 (YFP) reporter gene in germinating soybean cotyledons. Germinating soybean cotyledons were used as the target tissue for transient expression assays. Soybean seeds were rinsed with 10% Tween 20 in sterile water, surface sterilized with 70% ethanol for 2 minutes and then by 6% sodium hypochloride for 15 minutes. After rinsing the seeds were placed on wet filter paper in Petri dish to germinate for 4-6 days under light at 26° C. Green cotyledons were excised and placed inner side up on a 0.7% agar plate containing Murashige and Skoog media for particle gun bombardment. The DNA and gold particle mixtures were prepared similarly as described in EXAMPLE 5 except with more DNA (100 ng/μl). The bombardments were also carried out under similar parameters as described in EXAMPLE 5. YFP expression was checked under a Leica MZFLIII stereo microscope equipped with UV light source and appropriate light filters (Leica Microsystems Inc., Bannockburn, Ill.) and pictures were taken approximately 24 hours after bombardment with 8× magnification and the same camera settings as 1.06 gamma, 0.0% gain, and 0.58 second exposure.

The original full length EF1A promoter construct QC314, the full length construct with the attB2 gateway recombination site between the promoter and the YFP gene QC314-1Y, and the series of deletions QC314-2Y, 3Y, 4Y, 5Y, and 6Y all had strong yellow fluorescence signals in transient expression assay by showing the large green/yellow dots (shown as white dots in FIG. 6). The attB2 site did not seem to interfere with promoter activity and reporter gene expression. Each dot represented a single cotyledon cell which appeared larger if the fluorescence signal was strong or smaller if the fluorescence signal was weak even under the same magnification. The four longer deletions constructs QC314-2Y, 3Y, 4Y, 5Y had similar level of YFP expression as the full length construct QC314-1Y, indicating that the elements necessary for the EF1A promoter proper activity were retained in all these deletions. Interestingly, the shortest deletion construct QC314-6Y with only 175 bp promoter sequence upstream of the 5'UTR had the strongest fluorescence signal, indicating that the 175 bp sequence was long enough to retain strong promoter activity. Negative elements might exist upstream of the 175 bp region to further regulate the EF1A promoter activity. Removal of the 175 bp upstream sequence, resulting in the 5'UTR and 5'UTR intron construct QC314-7Y, caused most of the promoter activity to disappear. Only faint fluorescence signals were detected by the transient assay (FIG. 6). Construct pZSL90 with the constitutive promoter SCP1 driving the YFP expression and construct QC299i without any promoter driving the YFP expression were used in the transient assays as positive and negative controls, respectively. No fluorescence was detected in the negative control (picture not shown).

Example 8

EF1A:YFP Expression in Stable Transgenic Soybean Plants

YFP gene expression was tested at different stages of transgenic plant development for yellow fluorescence emission under a Leica MZFLIII stereo microscope equipped with a UV light source and appropriate fluorescent light filters (Leica Microsystems Inc.). Yellow fluorescence (shown as bright white areas in FIG. 7) was detected early on during somatic embryo development and throughout all stages of transgenic plant development in all tissues tested, such as somatic embryos, leaf, stem, root, flower, pod, and seed. During tissue culture stages of transgenic plant regeneration, fluorescence was uniformly detected in young globular and torpedo stage somatic embryos (FIG. 7A), in cotyledon stages embryos (FIG. 7B), and in mature and dried down embryos (FIG. 7C). Negative control embryos emitted weak red color (shown as dark grey areas in FIG. 7D) due to auto fluorescence from the chlorophyll contained in soybean green tissues including embryos. Negative controls for other tissue types displayed in FIG. 7 are not shown, but any green tissue such as leaf or stem, negative for YFP expression, would be red and any white tissue such as root, petal would be dark under the yellow fluorescent light filter.

When transgenic plantlets were regenerated from somatic embryos, yellow fluorescence was detected in leaf, stem, and root and was retained in all vegetative tissues throughout mature plants. Fluorescence in leaf was not as strong as in other tissues and fluorescence in the adaxial side of leaf (FIG. 7E) was not as strong as in the abaxial side (FIG. 7F). Veins had the strongest fluorescence in both sides of the leaf. Though trichomes on both sides of the leaf showed fluorescence, it was difficult to determine if the fluorescence signals were specific to the transgenic reporter gene since trichomes tended to fluoresce under different non-specific fluorescent light filters. Fluorescence was readily detected in stem and was strongest in the vascular bundles as shown by a stem cross section (FIG. 7G). Fluorescence was strong in all parts of root (FIG. 7H).

A soybean flower consists of five sepals, five petals including one standard large upper petal, two large side petals, and two small fused lower petals called kneel to enclose ten stamens and one pistil. The pistil consists of a stigma, a style, and an ovary in which there are 2-4 ovules. A stamen consists of a filament, and an anther on its tip. Pollen grains reside inside anther chambers and are released during pollination. Yellow fluorescence was detected in sepals and in the exposed part of petals of a young flower bud when its petals were still mostly enclosed by sepals (FIG. 7I). Fluorescence was detected in all parts including petals, anthers, filaments, and the pistil when a mature flower was dissected (FIG. 7J). Strong yellow fluorescence was detected in pollen grains which were still sticking to the anthers when a stamen was dissected and magnified (FIG. 7K). The stigma, style, ovary wall, and ovule inside the ovary of a dissected pistil all showed fluorescence though signals were not strong in the style and ovary wall (FIG. 7L).

Strong yellow fluorescence was detected in developing pods and seeds at all stages of the EF1A:YFP transgenic plants from very young R3 pod of ~5 mm long (FIG. 7M), to full R4 pod of ~20 mm long (FIG. 7N), until mature R5, R6 pod fully filled with seeds (FIG. 7O-P). Detail descriptions of soybean development stages can be found in (Fehr and Caviness, CODEN:IWSRBC 80:1-12 (1977)). Since T0 transgenic plants are hemizygous in nature, the embryos of their progeny T1 seeds will segregate according to Mendel's law, but the seed coats will not segregate since they are derived from the maternal tissue ovule coats. A positive T1 seed would have both its seed coat and embryo fluorescing (FIG. 7O). A negative T1 seed would only have its coat fluorescing but not its embryo (FIG. 7P). In conclusion, EF1A:YFP expression was detected with high levels in all tissues throughout transgenic plant development indicating that the soybean EF1A promoter is a strong constitutive promoter.

What is claimed is:

1. A recombinant DNA construct comprising a nucleotide sequence comprising any one of the sequences set forth in SEQ ID NO:1, SEQ ID NO:2, SEQ ID NO:3, SEQ ID NO:4, SEQ ID NO:5, SEQ ID NO:6 or SEQ ID NO:7, operably linked to at least one heterologous sequence, wherein said nucleotide sequence has constitutive promoter activity.

2. A vector comprising the recombinant DNA construct of claim 1.

3. A cell comprising the recombinant DNA construct of claim 1.

4. The cell of claim 3, wherein the cell is a plant cell.

5. A transgenic plant having stably incorporated into its genome the recombinant DNA construct of claim 1.

6. The transgenic plant of claim 5 wherein said plant is selected from the group consisting of dicotyledonous plants.

7. The plant of claim 6 wherein the plant is soybean.

8. A transgenic seed produced by the transgenic plant of claim 6, wherein the transgenic seed comprises the recombinant DNA construct.

9. A method of expressing a coding sequence or encodes a functional RNA in a plant comprising:

a) introducing the recombinant DNA construct of claim 1 into the plant, wherein the at least one heterologous sequence comprises a coding sequence or a functional RNA;

b) growing the plant of step a); and c) selecting a plant displaying expression of the coding sequence or the functional RNA of the recombinant DNA construct.

10. A method of transgenically altering a marketable plant trait, comprising:

a) introducing a recombinant DNA construct of claim 1 into the plant;

b) growing a fertile, mature plant resulting from step a); and c) selecting a plant expressing the at least one heterologous sequence in at least one plant tissue based on the altered marketable trait.

11. The method of claim 10 wherein the marketable trait is selected from the group consisting of: disease resistance, herbicide resistance, insect resistance carbohydrate metabolism, fatty acid metabolism, amino acid metabolism, plant development, plant growth regulation, yield improvement, drought resistance, cold resistance, heat resistance, and salt resistance.

12. A method for altering expression of at least one heterologous nucleic acid fragment in plant comprising:

(a) transforming a plant cell with the recombinant DNA construct of claim 1;

(b) growing fertile mature plants from transformed plant cell of step (a); and (c) selecting plants containing the transformed plant cell wherein the expression of the heterologous nucleic acid fragment is increased or decreased.

13. The method of claim 12 wherein the plant is a soybean plant.

14. A method for altering expression of at least one heterologous nucleic acid fragment in a plant comprising:

(a) transforming a plant cell with a recombinant expression construct comprising at least one heterologous nucleic acid fragment operably linked to the recombinant construct of claim 1;

(b) growing fertile mature plants from transformed plant cell of step (a); and (c) selecting plants comprising a transformed plant cell expressing the heterologous nucleic acid fragment during early seed development.

15. A method for expressing a yellow fluorescent protein ZS-YELLOW1 N1 in a host cell comprising:

(a) transforming a host cell with a recombinant expression construct comprising at least one ZS-YELLOW1 N1 (YFP) nucleic acid fragment operably linked to a promoter wherein said promoter consists of the nucleotide sequence set forth in SEQ ID NOs: 1 or 3; and (b) growing the transformed host cell under conditions that are suitable for expression of the recombinant DNA construct, wherein expression of the recombinant DNA construct results in production of increased levels of ZS-YELLOW1 N1 protein in the transformed host cell when compared to a corresponding nontransformed host cell.

16. A plant stably transformed with a recombinant expression construct comprising a soybean promoter and a heterologous nucleic acid fragment operably linked to said promoter, wherein said promoter is a capable of controlling expression of said heterologous nucleic acid fragment in a plant cell, and further wherein said promoter comprises any one of the sequences set forth in SEQ ID NO:1, SEQ ID NO:2, SEQ ID NO:3, SEQ ID NO:4, SEQ ID NO:5, SEQ ID NO:6 or SEQ ID NO:7.

17. The recombinant DNA construct according to claim 1, wherein the at least one heterologous sequence codes for a gene selected from the group consisting of: a reporter gene, a selection marker, a disease resistance conferring gene, a herbicide resistance conferring gene, an insect resistance conferring gene; a gene involved in carbohydrate metabolism, a gene involved in fatty acid metabolism, a gene involved in amino acid metabolism, a gene involved in plant development, a gene involved in plant growth regulation, a gene involved in yield improvement, a gene involved in drought resistance, a gene involved in cold resistance, a gene involved in heat and salt resistance in plants.

18. The recombinant DNA construct according to claim 1, wherein the at least one heterologous sequence encodes a protein selected from the group consisting of: a reporter protein, a selection marker, a protein conferring disease resistance, protein conferring herbicide resistance, protein conferring insect resistance; protein involved in carbohydrate metabolism, protein involved in fatty acid metabolism, protein involved in amino acid metabolism, protein involved in plant development, protein involved in plant growth regulation, protein involved in yield improvement, protein involved in drought resistance, protein involved in cold resistance, protein involved in heat resistance and salt resistance in plants.

* * * * *